United States Patent
Gilboa-Geffen et al.

(10) Patent No.: US 11,591,557 B2
(45) Date of Patent: Feb. 28, 2023

(54) SYSTEMS FOR ALLERGEN DETECTION

(71) Applicant: DOTS Technology Corp., Natick, MA (US)

(72) Inventors: Adi Gilboa-Geffen, Wayland, MA (US); Gregory J. Kintz, Santa Cruz, CA (US); Adam J. Young, Dedham, MA (US); Patrick Murphy, Allston, MA (US); Joshua Glenn Anthony, Reading, MA (US); Paul Fleming, Santa Clara, CA (US); Brett Gorham, Santa Cruz, CA (US); Ryan Griswold, Los Gatos, CA (US); Bruce Richardson, Los Gatos, CA (US)

(73) Assignee: DOTS Technology Corp., Natick, MA (US)

( * ) Notice: Subject to any disclaimer, the term of this patent is extended or adjusted under 35 U.S.C. 154(b) by 814 days.

(21) Appl. No.: 16/487,450

(22) PCT Filed: Feb. 21, 2018

(86) PCT No.: PCT/US2018/018881
§ 371 (c)(1),
(2) Date: Aug. 21, 2019

(87) PCT Pub. No.: WO2018/156535
PCT Pub. Date: Aug. 30, 2018

(65) Prior Publication Data
US 2020/0071647 A1 Mar. 5, 2020

Related U.S. Application Data

(60) Provisional application No. 62/461,332, filed on Feb. 21, 2017.

(51) Int. Cl.
*C12M 3/06* (2006.01)
*C12M 1/32* (2006.01)
(Continued)

(52) U.S. Cl.
CPC ............ *C12M 23/16* (2013.01); *C12M 23/12* (2013.01); *G01J 3/42* (2013.01); *G01J 3/4406* (2013.01);
(Continued)

(58) Field of Classification Search
CPC ......... C12M 23/16; C12M 23/12; G01J 3/42; G01J 3/4406; G01N 21/51; G01N 21/53;
(Continued)

(56) References Cited

U.S. PATENT DOCUMENTS 5,250,186 A 10/1993 Dollinger et al.
2002/0109844 A1 8/2002 Christel et al.
(Continued)

FOREIGN PATENT DOCUMENTS

CA 2928644 A1 5/2015
CN 204287185 U 4/2015
(Continued)

OTHER PUBLICATIONS

International Search Report and Written Opinion for corresponding PCT Application No. PCT/US2018/018881 entitled "Systems for Allergen Detection" dated Jun. 25, 2018.
(Continued)

*Primary Examiner* — David P Porta
*Assistant Examiner* — Gisselle M Gutierrez
(74) *Attorney, Agent, or Firm* — Choate, Hall & Stewart LLP; Brenda Herschbach Jarrell; Peter A. Flynn

(57) ABSTRACT

The present invention is drawn to devices and systems for allergen detection in a sample. The allergen detection system includes a sampler, a disposable analysis cartridge and a detection device with an optimized optical system. In some embodiments, the allergen detection utilizes aptamer nucleic acid molecules as detection agents. In some embodiments,
(Continued)

the nucleic acids are conjugated to magnetic beads or solid surfaces such as glasses, microwells and microchips.

29 Claims, 29 Drawing Sheets

(51) Int. Cl.
| | |
|---|---|
| *G01J 3/42* | (2006.01) |
| *G01J 3/44* | (2006.01) |
| *G01N 21/51* | (2006.01) |
| *G01N 21/53* | (2006.01) |
| *G01N 21/64* | (2006.01) |
| *G01N 33/02* | (2006.01) |
| *G01N 21/17* | (2006.01) |

(52) U.S. Cl.
CPC ............. *G01N 21/51* (2013.01); *G01N 21/53* (2013.01); *G01N 21/645* (2013.01); *G01N 33/02* (2013.01); *G01N 2021/174* (2013.01); *G01N 2021/1744* (2013.01); *G01N 2021/6419* (2013.01); *G01N 2021/6491* (2013.01)

(58) Field of Classification Search
CPC ................. G01N 21/645; G01N 33/02; G01N 2021/174; G01N 2021/1744; G01N 2021/6419; G01N 2021/6491; G01N 1/08; G01N 33/5308; G01N 33/582; G01N 21/6428; G01N 33/54326; G02B 5/20
See application file for complete search history.

(56) References Cited

U.S. PATENT DOCUMENTS

| | | |
|---|---|---|
| 2004/0191786 A1 | 9/2004 | Yue et al. |
| 2007/0281288 A1 | 12/2007 | Belkin et al. |
| 2008/0180259 A1 | 7/2008 | Jung et al. |
| 2008/0181821 A1 | 7/2008 | Jung et al. |
| 2009/0211345 A1 | 8/2009 | Nahm et al. |
| 2010/0151474 A1 | 6/2010 | Afanasyev et al. |
| 2011/0201099 A1 | 8/2011 | Anderson et al. |
| 2014/0275869 A1 | 9/2014 | Kintz et al. |
| 2016/0209420 A1 | 7/2016 | Barnes et al. |
| 2016/0216287 A1 | 7/2016 | Holmes et al. |
| 2018/0154350 A1* | 6/2018 | Gilboa-Geffen ... G01N 33/5308 |

FOREIGN PATENT DOCUMENTS

| | | |
|---|---|---|
| CN | 104707674 A | 6/2015 |
| TW | 200806691 A | 2/2008 |
| WO | 2012078455 A1 | 6/2012 |
| WO | 2014164933 A1 | 10/2014 |
| WO | 2015066027 A2 | 5/2015 |
| WO | 2016149253 A1 | 9/2016 |
| WO | 2017160616 A1 | 9/2017 |
| WO | 2018089391 A1 | 5/2018 |
| WO | 2018156535 A1 | 8/2018 |

OTHER PUBLICATIONS

Office Action dated Mar. 25, 2022 in corresponding Taiwan Application 107105761 entitled Systems for Allergen Detection.
Office Action dated Mar. 30, 2022 in corresponding Singapore Application 11201907541T entitled Systems for Allergen Detection.
Office Action dated Feb. 7, 2022 in corresponding Chinese application 201880013163X entitled Systems for Allergen Detection.

* cited by examiner

FIG. 6A
FIG. 6B
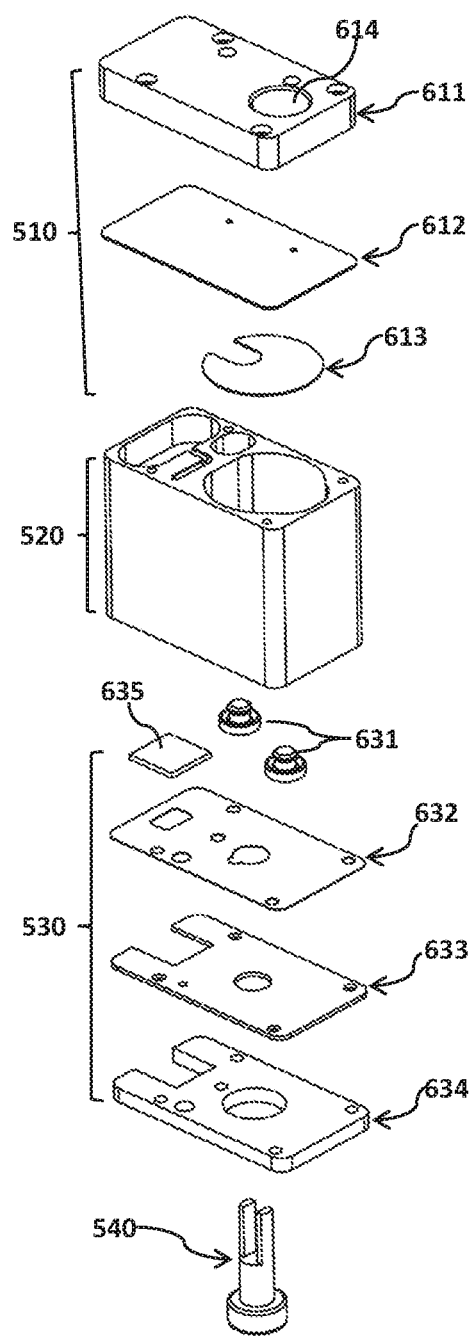
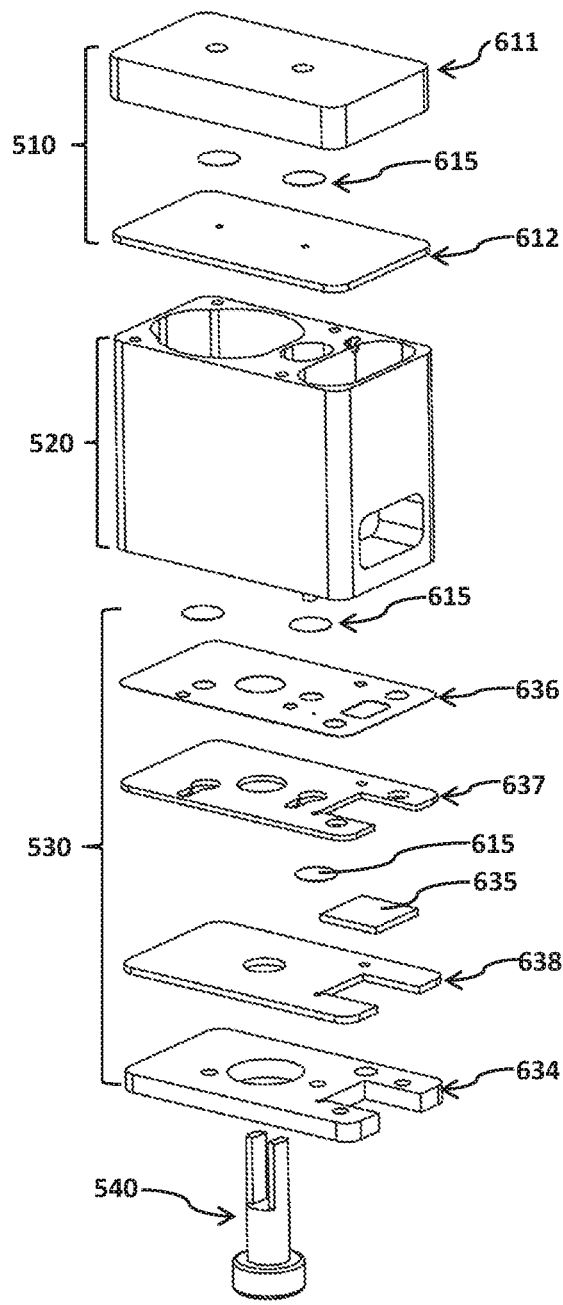

SYSTEMS FOR ALLERGEN DETECTION

CROSS REFERENCE TO RELATED APPLICATIONS

This application is a 35 U.S.C. § 371 U.S. National Stage Entry of International Application No. PCT/US2018/018881 filed Feb. 21, 2018, which claims the benefit of priority of U.S. Provisional Patent Application No. 62/461,332, filed Feb. 21, 2017, entitled "SYSTEMS FOR ALLERGEN DETECTION", the contents of each of which are herein incorporated by reference in their entirety.

FIELD OF THE INVENTION

The present invention is drawn to devices and systems for allergen detection in food samples.

BACKGROUND OF THE INVENTION

Allergy (e.g., food allergy) is a common medical condition that can have lethal consequences. It has been estimated that in the United States, up to 2 percent of adults and up to 8 percent of children, particularly those under three years of age, suffer from food allergies (about 15 million people), and this prevalence is believed to be increasing. Detection of allergens is not always straightforward and thus, a portable device that enables a person who has food allergy to test their food and determine accurately and immediately the allergen content will be of great benefit to provide for an informed decision on whether to consume or not.

Researchers have tried to develop suitable devices and methods to meet this need, such as those devices and systems disclosed in U.S. Pat. No. 5,824,554 to McKay; US Patent Application Pub. No.: 2008/0182339 and U.S. Pat. No. 8,617,903 to Jung et al.; US Patent Application Pub. No.: 2010/0210033 to Scott et al: U.S. Pat. No. 7,527,765 to Royds; U.S. Pat. No. 9,201,068 to Suni et al.; and U.S. Pat. No. 9,034,168 to Khattak and Sever, the contents of each of which are incorporated herein by reference in their entirety. There is still a need for improved molecule detection technologies. There is also a need for devices and systems that detect allergens of interest in less time, with high sensitivity and specificity, and with less technical expertise than the devices used today.

The present inventors have developed detection systems and devices using nucleic acid aptamer based signal polynucleotides (SPNs) as detection agents to detect an allergen in a test sample. The detection agents may be conjugated to magnetic beads and/or solid surfaces (e.g., a glass) to form allergen detection sensors; the sensors may then be integrated into an instrument for operating the detection assay, for example, a detection device as disclosed in the present invention. The aptamers that specifically bind to a target allergen may be those disclosed in commonly owned U.S. Provisional Application Ser. No. 62/418,984, filed on Nov. 8, 2016; and 62/435,106, filed on Dec. 16, 2016; 62/512,299 filed on May 30, 2017; and the PCT application No. PCT/US2017/060487 filed on Nov. 8, 2017; the contents of each of which are incorporated herein by reference in their entirety.

The inventors of the present invention further developed detection systems which include a separate sampler, disposable cartridges/vessels and a detection instrument, for fast and accurate detection of an allergen(s) in a sample using aptamer-based signal polynucleotides (SPNs). Particularly the aptamers and/or aptamer complement complexes are conjugated to magnetic beads and/or solid surfaces. The magnetic beads and solid surfaces coated with aptamer ligands are then used as detection sensors. The sensors may be integrated into the disposable cartridges of the present invention. They may also be used in other detection systems. Such devices may be used by consumers in non-clinical settings, for example in the home, in restaurants and school cafeteria.

SUMMARY OF THE INVENTION

The present invention provides systems, devices, disposable vessels/cartridges, optical modules and methods for use in allergen detection in various types of samples, in particular, food samples. The allergen detection devices and systems are portable and handheld. In one aspect, the dimensions of the systems and devices may be less than 6 inches.

One aspect of the present invention is directed to an allergen detection system for detecting the presence and/or absence of one or more allergens in a food sample. In various embodiments, the system comprises: (a) means for collecting a test sample; (b) at least one disposable detection vessel/cartridge (as used herein, the terms "vessel" and 'cartridge" and "test cup" are used interchangeably) for receiving and processing the test sample, and analyzing the interaction between an allergen(s) in the test sample and the detection agents; and (c) a detection device for reading detection signals and detecting the allergen(s) in the test sample. The detection device may be removably connected to the disposable cartridge. In some aspects, the assay further comprises a step of washing and re-suspending the magnetic beads when they are used as the sensors for detecting the target allergen.

In some embodiments, a separate sampler may provide means for collecting a test sample. In one embodiment, the sampler is a separate food corer for collecting a food sample. The food corer may be configured for measuring a sized portion of a food sample and/or pre-processing the collected food sample. The food corer may have a distal portion provided with a corer top cap at the distal end and a proximal portion provided with a cutting edge at the distal end which is configured to pick a food sample and pre-process the picked sample.

In one embodiment, the food corer comprises a plunger having a distal end connecting to the corer top cap and a proximal plunger tip with a seal, a handle and a corer configured for holding the test sample being picked.

In some embodiments, the detection cartridge is disposable, suitable for one particular allergen. The detection cartridge comprises at least one homogenization chamber and at least one detection/reaction chamber where the detection reaction occurs. In one aspect of the invention, the detection cartridge may be a disposable test cup or cup-like container. The disposable test cup or cup-like container may be constructed as an analytical module in which a test sample is processed and an allergen of interest in the test sample is detected through the interaction with detection agents. In some aspects, the disposable test cup or cup-like container comprises a cup body, a cup bottom and a cup lid. The test cup may be divided into several compartments specialized for various functions, including homogenization, buffer storage, waste collection, allergen reaction and signal detection.

In some embodiments, the reaction and signal detection chamber may comprise a specialized area which is configured for holding a detection sensor specific for a target allergen. In some aspects, the detection sensor may be magnetic beads conjugated with aptamers that bind to the target allergen. The aptamers or their complements may be attached to the magnetic beads directly or through any other anchors and linkers. In other aspects, the detection sensor may be a solid support of which the surface is coated with aptamers that bind to the target allergen. In one embodiment, the specialized sensing area within the reaction and signal detection chamber may be a fluidic chip comprising a flow cell; the flow cell is configured for holding magnetic beads. The reaction and signal detection chamber may comprise at least one optical window. In one embodiment, the chamber comprises two optical windows, one primary optical window configured for reading optical signals and one secondary optical window configured for reading light absorption or reading both light absorption and scattered light. In other embodiments, the chamber may comprise a separate window configured for reading scattered light.

The detection device of the present invention comprises (a) an external housing that provides support for the components of the detection device; (b) a mate plane or receptacle for coupling a detection cartridge (e.g., a disposable test cup or cup-like container) when implementing an allergen detection testing, and (c) means integrated for operating an allergen detection testing; and an optional plug for power supply.

In accordance with the present invention, the components of the detection device that are integrated for operating an allergen detection testing include (i) means for processing a test sample comprising a homogenizer; (ii) means for driving and controlling the homogenization; (iii) means for driving and controlling the flow of the processed sample during the process of an allergen detection testing; (iv) an optical system for detecting a reaction signal; and (v) means for visualizing a detection result including means of converting and digitizing the detection signal and a display window; and (vi) a power supply.

In some embodiments, means for driving the liquid flow and controlling the flow rate mayx be a pump or an external pressure. The pump may be a gas or air pump, or an equivalent thereof. The processed sample solution is flowed into a plurality of chambers within the detection cartridge (e.g., the test cup or cup-like container) during a detection assay.

In some embodiments, the optical system mayx comprise excitation optics, emission optics, scatter optics and absorption optics.

In some embodiments, a printed circuit board (PCB) is connected directly or indirectly to the optical system for displaying the testing readout. The result may be displayed as numbers, icons, colors and/or letters, or other equivalents.

Another aspect of the present invention relates to an allergen detection testing assay for detection of the allergen content in a sample comprising the steps of (a) obtaining a test sample suspected of containing an allergen(s) of interest, (b) homogenizing the obtained sample and extracting allergen proteins using an extraction buffer, (c) contacting the processed sample with a detection sensor which comprises magnetic beads or solid surfaces coated with aptamers and/or aptamer-complement complexes that specifically bind to a target allergen; (d) determining a fluorescence signal arising from the contacting step in (c); and (e) processing and digitizing the detected signals and visualizing the interaction between the detection agents and the allergen(s).

In some embodiments, the detection system may comprise a user interface that may be accessed and controlled by a software application. The software may be run by a software application on a personal device such as a smartphone, a tablet computer, a personal computer, a laptop computer, a smartwatch and/or other devices. In some cases, the software may be run by an internet browser. In some embodiments, the software may be connected to a remote and localized server referred to as the cloud.

BRIEF DESCRIPTION OF THE DRAWINGS

FIG. 6A and FIG. 6B illustrate exploded views of two different embodiments of the disposable test cup 300.

DETAILED DESCRIPTION OF THE INVENTION

Figure 1:
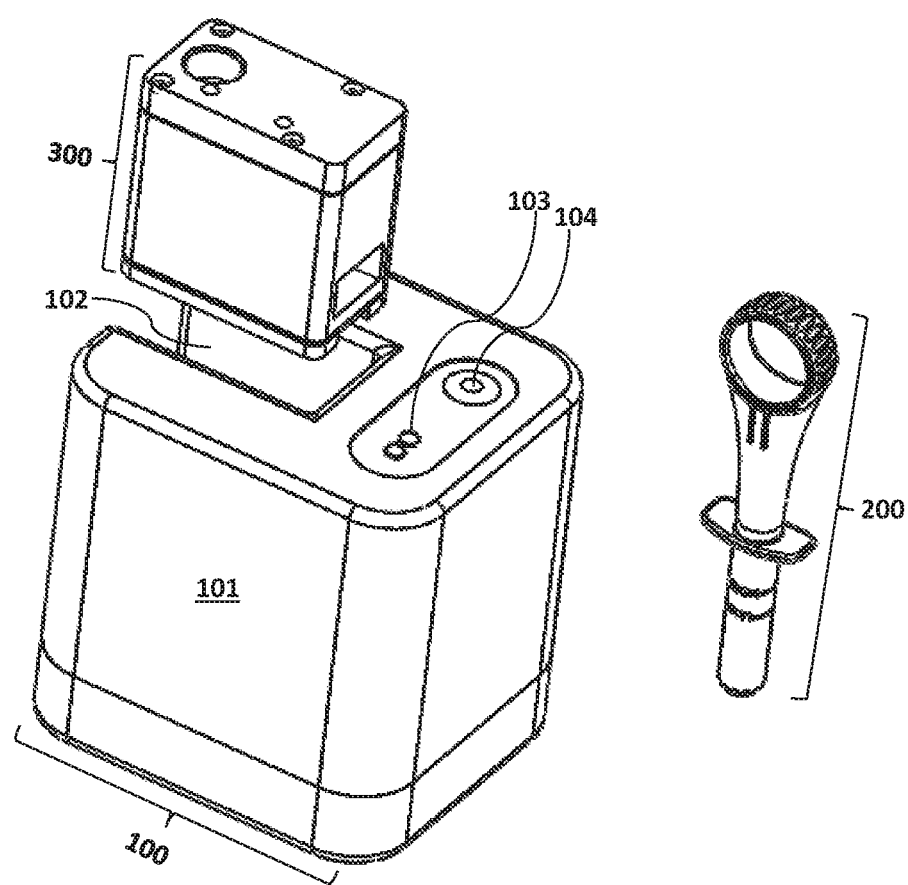
FIG. 1 is an embodiment of a detection system in accordance with the present invention comprising a detection device 100 having an external housing 101 and a mate plane or receptacle 102 configured for holding the disposable test cup 300, a separate food corer 200 as an example of the sampler, a disposable test cup 300 as an example of the detection cartridge. Optionally, an execution/action button 104 that allows a user to execute an allergen detection testing and a display window 103 may be included.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or constructing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention. Unless defined otherwise, all technical and scientific terms used herein have the same meaning as commonly understood by one of ordinary skill in the art to which this invention belongs. In the case of conflict, the present description will control.

The use of analytical devices to ensure food safety has not yet advanced to the point of fulfilling its promise. In particular, portable devices based on simple, yet accurate, sensitive and rapid detection schemes have not yet been developed for detection of the wide variety of known allergens. One of the more recent reviews of aptamer-based analysis in the context of food safety control indicated that while a great variety of commercial analytical tools have been developed for allergen detection, most of them rely on immunoassays. It was further indicated that the selection of aptamers for this popular allergens is emerging (Amaya-Gonzalez et al., *Sensors* 2013, 13, 16292-16311, the contents of which are incorporated herein by reference in their entirety).

The present invention provides detection systems and devices that can specifically detect low concentrations of allergens in a variety of food samples. The present detection systems, devices and methods use nucleic acid molecule (i.e., aptamers) based detection sensors to bind and detect a target allergen presented in a sample. The nucleic acid agents may be aptamers alone, or aptamers complexed with short complementary sequences. In particular, the detection agents may be attached to a solid support such as the surface of a magnetic particle, silica, agarose particles, polystyrene beads, a glass surface, a microwell, a chip (e.g., a microchip), or the like. The magnetic beads and solid surfaces having surface bound detection agents form the detection sensors of the present detection systems. It is within the scope of the present invention that such sensors can also be integrated into any suitable detection systems and instruments for similar purpose.

In one embodiment, the detection system and/or device of the present invention is a miniaturized, portable and handheld product, which is intended to have a compact size which enhances its portability and discreet operation. A user can carry the detection system and device of the present invention and implement a rapid and real-time testing of the presence and/or absence of one or more allergens in a food sample, prior to consuming the food. The detection system and device, in accordance with the present invention, can be used by a user at any location, such as at home or in a restaurant.

In one embodiment, the detection system and/or device displays the testing result as a standard readout and the detection can be implemented by any user following the simple instructions on how to operate the detection system and device.

In some embodiments, the detection system and device is constructed for simple, fast, and sensitive one-step execution. The system may complete an allergen detection testing in less than 5 minutes, or less than 4 minutes, or less than 3 minutes, or less than 2 minutes, or less than 1 minute. In some aspects, the allergen detection may be completed in approximately 60 seconds, 55 seconds, 50 seconds, 45 seconds, 40 seconds, 35 seconds, 30 seconds, 25 seconds, 20 seconds, or 15 seconds.

In accordance with the present invention, the detection system and device may involve a mechatronic construction process integrating electrical engineering, mechanical engineering and computing engineering to implement and control the process of allergen detection testing, including rechargeable or replaceable batteries, motor drivers for processing the test sample, pumps or actuators for controlling the flow of the processed sample solution to different components of the detection device, and connectors that couple and integrate different components for fast allergen testing. The detection device of the present invention also includes an optical system which is configured for detection of the presence and concentration of an allergen of interest in a test sample and conversion of detection signals into readable signals; a magnet system for operating the detection sensor; and a housing which provides support for other parts of the detection device and integrates different parts together as a functional product.

In some embodiments, the detection system and/or device is constructed such that the disposable detection cartridges (e.g., disposable test cups or cup-like containers), unique to one or more specific allergens, are constructed for receiving and processing a test sample, and assaying the detection test, in which all required buffer solutions are packed. Therefore, all buffer solutions may be confined in the disposable cup or cup-like container. As a non-limiting example, a disposable peanut test cup may be used to detect peanut in any food sample by a user and discarded after the testing. This prevents cross-contamination when different allergen tests are performed in the same device.

In some embodiments, a separate sampler that can measure and size a test sample is provided. In one aspect, the sampler can further pre-process the test sample, such as cutting the sample into small pieces, blending, abrading and/or grinding, to make the sample suitable for allergen protein extraction.

Detection Systems

In general, an allergen detection system of the present invention comprises at least one sampler for collecting a test sample, at least one disposable detection cartridge for implementing an allergen detection test, and a detection device for detecting and visualizing the result of the detection test.

Figure 15:
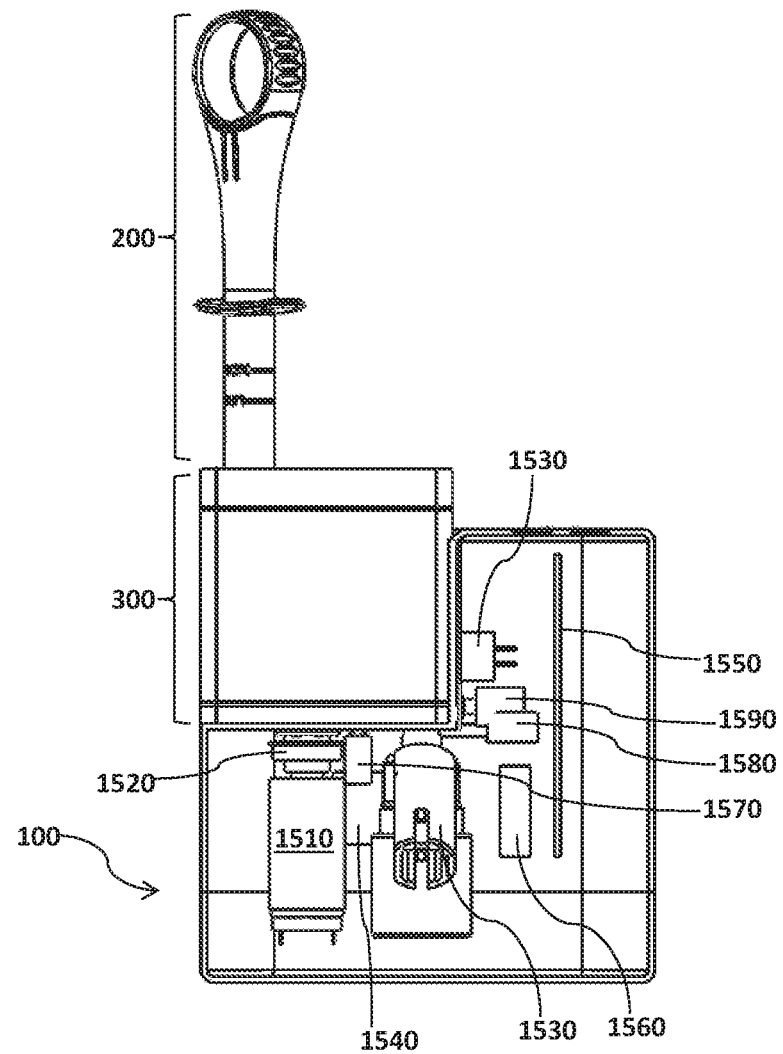
FIG. 15 illustrates a view of the detection device 100 when different components are assembled and integrated as a functional device with the food corer 200 and the test cup 300.

As shown in FIG. 1, an embodiment of the detection system of the present invention comprises a detection device 100 configured for processing a test sample, implementing an allergen detection test, and detecting and reporting the result of the detection test, a separate food corer 200 as an example of the sampler, and a disposable test container/cartridge 300 as an example of the detection cartridge. In one example, the disposable test cartridge may be a cup or a cup-like container 300. The detection device 100 includes an external housing 101 that provides support to the components (as shown in FIG. 15) of the detection device 100. A primary mate plane or receptacle 102 of the detection device 100 is constructed for docking the disposable test cup 300. The external housing 101 also provides surface space for buttons to operate the device 100. An execution/action button 104 that allows a user to execute an allergen detection test and a display window 103 may be included. Optionally a cover (not shown) may be present to cover the test cup 300 during the test.

Figure 2:
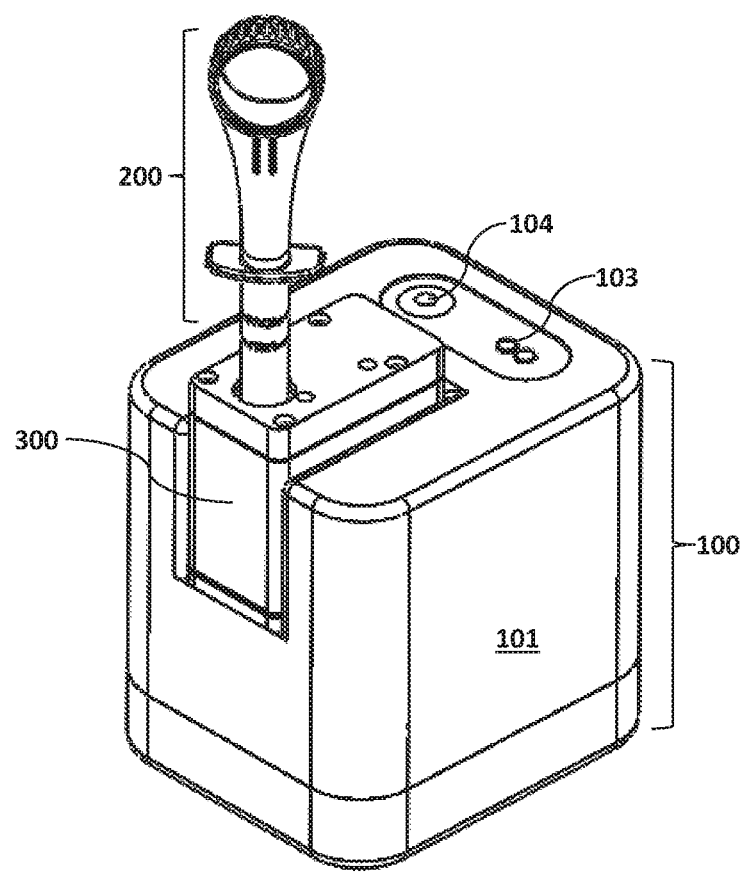
FIG. 2 illustrates an assembly of the detection system shown in FIG. 1 during the process of implementing an allergen detection testing.

During the process of implementing an allergen detection test, the food corer 200 holding a sample is inserted into the disposable test cup 300 and the disposable test cup 300 is inserted into the mate plane or receptacle 102 of the detection device 100 for detection, as shown in FIG. 2.

The assembly of the detection system shown in FIG. 2 is not intended to be limiting. Other ways to assemble the disposable test cup 300, the food corer 200 and the detection device 100 are within the scope of the present invention.

Sampler

Collecting an appropriately sized sample is an important step for implementing allergen detection testing. In some embodiments of the present invention, a separate sampler for picking up and collecting test samples (e.g. food samples) is provided. In one aspect, a coring-packer-plunger concept for picking up and collecting a food sample is disclosed herein. Such a mechanism may measure and collect one or several sized portions of the test sample and provide pre-processing steps such as cutting, grinding, abrading and/or blending, for facilitating the homogenization and extraction or release of allergen proteins from the test sample. According to the present invention, a separate food corer 200 is constructed for obtaining different types of food samples and collecting an appropriately sized portion of a test sample.

Figure 3A:
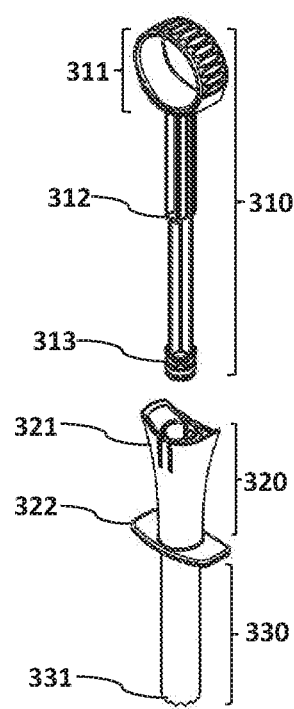
FIG. 3A illustrates an embodiment of the food corer 200 as an example of the sampler.

As shown in FIG. 3A, the food corer 200 may comprise three parts: a plunger 310 at the distal end, a handle 320 configured for coupling a corer 330 at the proximal end. The plunger 310 has a distal portion provided with a corer top grip 311 (FIG. 3A) at the distal end, which facilitates the user to maneuver the plunger 310 up and down, a plunger stop 312 in the middle of the plunger body, and a seal 313 at the proximal end of the plunger body. The handle 320 may comprise a snap fit 321 at the distal end and a skirt 322 at the proximal end connecting to the corer 330. The corer 330 mayx comprise a proximal portion provided with a cutting edge 331 at the very proximal end (FIG. 3A). The corer 330 is configured for cutting and holding the collected sample to be expelled into the disposable test cup 300.

Figure 3B:
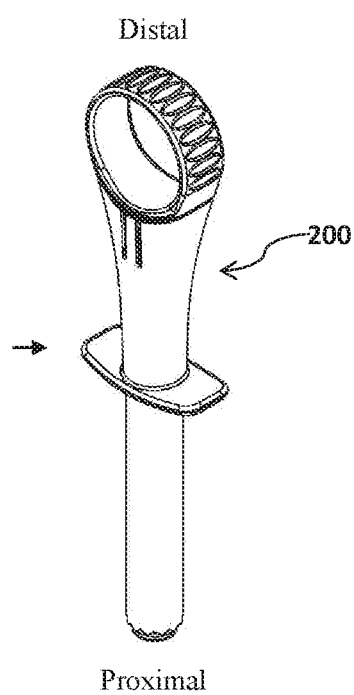
FIG. 3B illustrates a sampler assembly 200.

In one embodiment, the plunger 310 may be inserted inside the corer 330, where the proximal end of the plunger 310 may protrude from the corer 330 for directly contacting a test sample, and together with the cutting edge 331 of the corer 330, picking up a sized portion of the test sample (FIG. 3B). In accordance with the present invention, the plunger 310 is used to expel sampled food from the corer 330 into the disposable test cup 300, and to pull certain foods into the corer 330 as well, such as liquids and creamy foods. The feature of the plunger stop 312, through an interaction with the snap fit 321, may prevent the plunger 310 from being pulled back too far or out of the corer body 330 during sampling. The seal 313 at the very proximal end of the plunger 310 may maintain an air-tight seal in order to withdraw liquids into the corer 330 by means of pulling the plunger 310 back. In some embodiments, the plunger 310 may be provided with other types of seals including a molded feature, or a mechanical seal. The handle 320 is constructed for a user to hold the coring component of the sampler 200. For example, the skirt 322 gives the user means for operating the food sampler 200, pushing down the corer 330 and driving the corer 330 into the food sample to be collected.

Figure 4A:
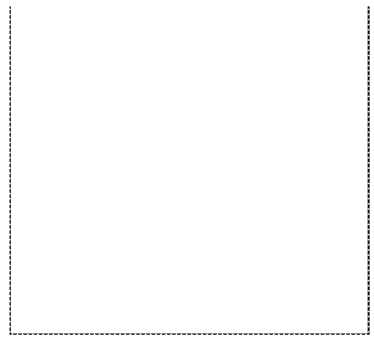
FIGS. 4A to 4F illustrate exemplary embodiments of the cutting edge 331.
Figure 4B:
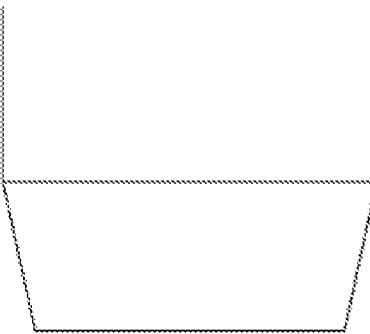
Figure 4C:
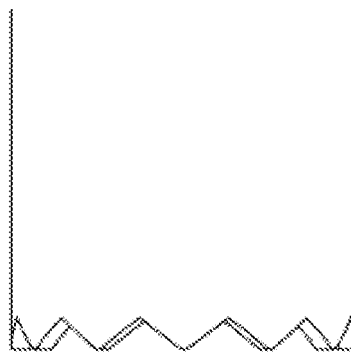
Figure 4D:
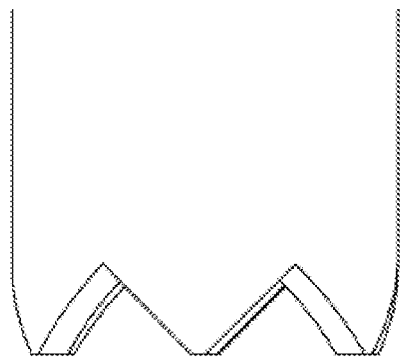
Figure 4E:
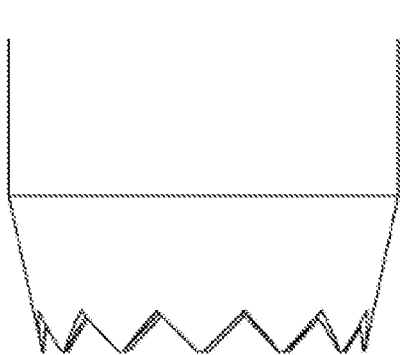
Figure 4F:
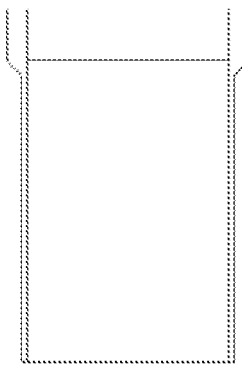

In some aspects, the cutting edge 331 may be configured for pre-processing the collected sample, allowing the sampled food to be cored in a pushing, twisting and/or cutting manner. As some non-limiting examples, the cutting edge 331 may be a flat edge (FIG. 4A), a sharp edge (FIG. 4B), a serrated edge with various numbers of teeth (FIGS. 4C and 4D), a sharp serrated edge (FIG. 4E) or a thin wall edge (FIG. 4F). In other aspects, the inside diameter of the corer 330 varies, ranging from about 5.5 mm to 7.5 mm. Preferably the inside diameter of the corer 330 may be from about 6.0 mm to about 6.5 mm. The inside diameter of the corer 330 may be 6.0 mm, 6.1 mm, 6.2 mm, 6.3 mm, 6.4 mm, 6.5 mm, 6.6 mm, 6.7 mm, 6.8 mm, 6.9 mm, or 7.0 mm. The size of the corer 330 is optimized for a user to collect the right amount of the test sample (e.g., 0.5 mg).

The parts of the food corer 200 may be constructed as any shape for easy handling such as triangular, square, octagonal, circular, oval, and the like.

In other embodiments, the food corer 200 mayx be further provided with a means for weighing a test sample being picked up, such as a spring, a scale or the equivalent thereof. As a non-limiting example, the food corer 200 may be provided with a weigh tension module.

The food corer 200 may be made of plastic materials, including but not limited to, polycarbonate (PC), polystyrene (PS), poly(methyl methacrylate) (PMMA), polyester (PET), polypropylene (PP), high density polyethylene (HDPE), polyvinylchloride (PVC), thermoplastic elastomer (TPE), thermoplastic urethane (TPU), acetal (POM), polytetrafluoroethylene (PTFE), or any polymer, and combinations thereof.

Disposable Detection Cartridge

In accordance with the present invention, at least one separate detection cartridge is provided as part of the detection system. The detection cartridge is disposable and used for a particular allergen(s). A disposable detection cartridge is constructed for dissociation of food samples and allergen protein extraction, filtration of food particles, storage of reaction solutions/reagents and detection agents, capture of an allergen of interest using detection sensors such as magnetic beads and solid support with bound detection agents such as antibodies and nucleic acid molecules that specifically bind to allergen proteins. In one aspect, the detection agents are nucleic acid molecules such as SPNs, aptamers or aptamer-complement complexes. Examples of such detection agents are described, for example in U.S. Provisional Application Ser. No. 62/418,984, filed on Nov. 8, 2016; 62/435,106, filed on Dec. 16, 2016; and 62/512,299 filed on May 30, 2017; and the PCT application No. PCT/US2017/060487 filed on Nov. 8, 2017; which are commonly owned and incorporated herein by reference in their entirety.

In some embodiments, a disposable detection cartridge is intended to be used only once for allergen testing in a sample and therefore may be made of low cost plastic materials, for example, transparent high density polyethylene (HDPE), polycarbonate (PC), poly(methyl methacrylate) (PMMA), polypropylene (PP), polyvinylchloride (PVC), polystyrene (PS), polyester (PET), or other thermoplastics. Accordingly, a disposable detection cartridge may be constructed for any particular allergen of interest. In some embodiments, these disposable cartridges may be constructed for one particular allergen only, which may avoid cross contamination with other allergen reactions.

In other embodiments, these disposable cartridges may be constructed for detecting two or more different allergens in a test sample in parallel. In some aspects, the disposable cartridges may be constructed for detecting two, three, four, five, six, seven, or eight different allergens in parallel. In one aspect, the presence of multiple allergens, e.g., two, three, four, five, or more, are detected simultaneously, a positive signal may be generated indicating which allergen is present. In another aspect, a system is provided to detect if an allergen, e.g., peanut or a tree-nut, is present and generate a signal to indicate the presence of such allergen.

Figure 5A:
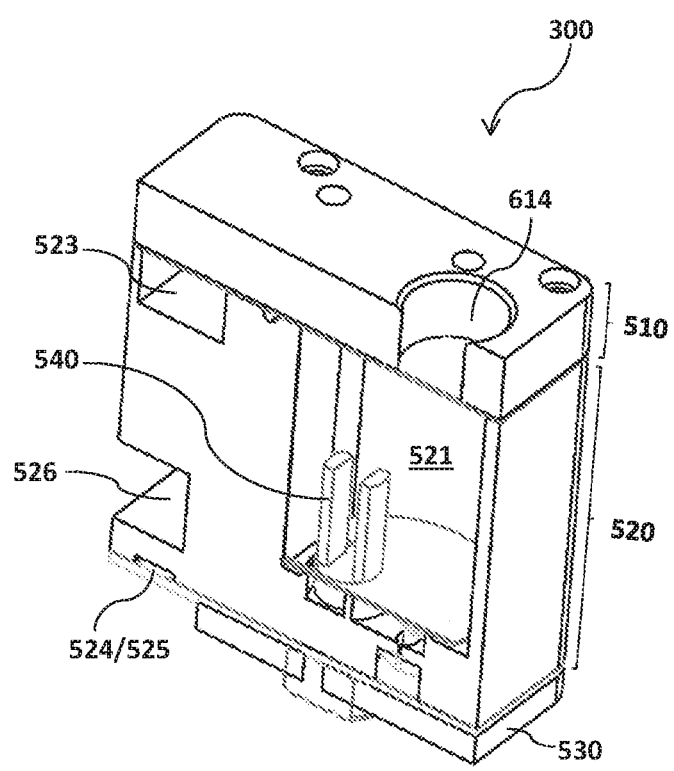
FIG. 5A illustrates an embodiment of a disposable test cup 300 in a side view, comprising a cup top cover 510, a cup body 520, a cup bottom 530 and a rotor 540.

The disposable detection cartridge may be a disposable test cup or a cup-like container. According to one embodiment of the test cup, as shown in FIG. 5A, the assembled disposable test cup 300 includes a cup top cover 510, a cup body 520 for receiving a test sample, processing the test sample and contacting/mixing the processed sample with the detection agents (e.g., aptamer-magnetic bead conjugates), a cup bottom assembly 530 and a homogenization rotor 540.

Figure 5B:
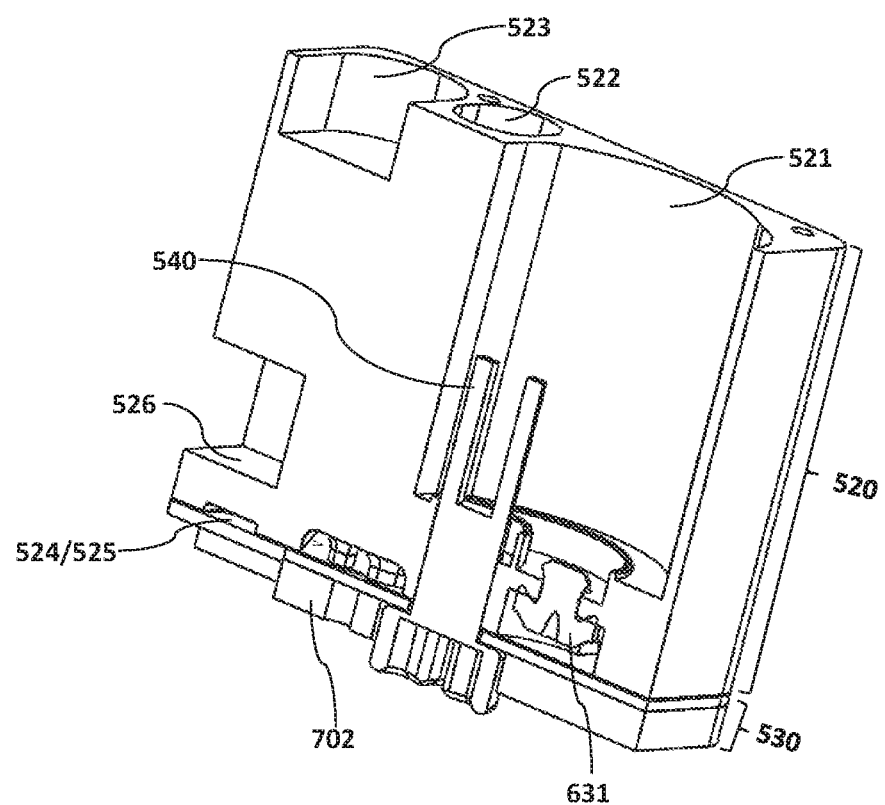
FIG. 5B is a section view of the test cup 300, demonstrating one embodiment of the configurations inside the cup body 520: the homogenization chamber 521, wash buffer storage chamber 522, waste chamber 523, and reaction and signal detection chamber 524 having a primary optical window 525 and a secondary optical window 526.
Figure 9:
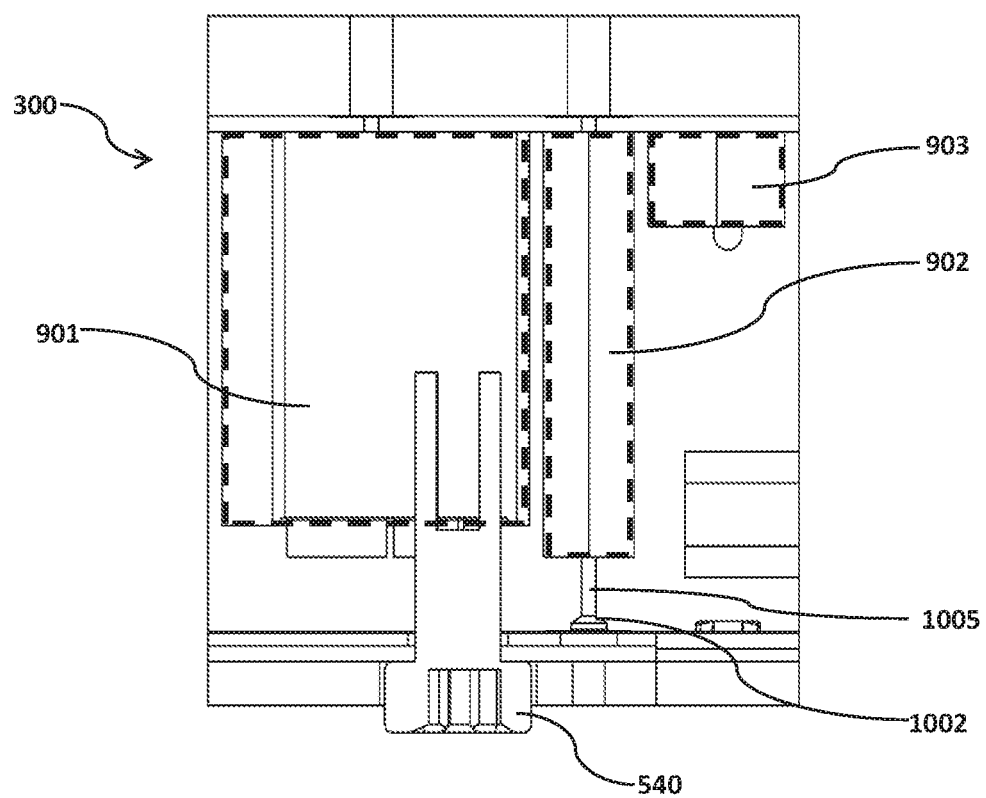
FIG. 9 indicates the positions of the fluid storage reservoirs within the test cup 300.

The test cup body 520 may include a plurality of chambers. In one embodiment, the test cup body 520 includes one homogenization chamber 521 comprising a food processing reservoir 901 (as shown in FIG. 9), a wash buffer storage chamber 522 comprising wash buffer storage reservoir 902 (as shown in FIG. 9), a waste chamber 523 comprising a waste reservoir 903 (as shown in FIG. 9), and a reaction chamber 524 (also called a signal detection chamber) (FIGS. 5A and 5B). All the analytical reactions occur in the reaction chamber 524. The reaction chamber 524 is the place where a homogenized and processed sample is mixed with the detection agents pre-stored within the test cup 300 and a detectable signal (e.g., a fluorescence signal) is generated. In alternative embodiments, more than one buffer storage reservoir may be included in the buffer storage chamber 522. As a non-limiting example, the extraction buffer may be stored separately in a reservoir within the buffer storage chamber 522, instead of being pre-stored in the food processing reservoir 901.

FIG. 6A shows an exploded view of the disposable test cup 300. In one embodiment, the disposable test cup 300 may comprise a top cover 510 that includes a cup lid 611 having a food corer port 614 for receiving a food corer 200, a gasket 612 and a seal membrane (not shown in FIG. 6A) between the cup lid 611 and gasket 612 and the cup body 520. The seal membrane may be a foil seal 615 as shown in FIG. 6B. A filter membrane(s) or a filter assembly 613 may also be included in the top cover 510 (FIG. 6A). The cup bottom assembly 530 includes at least one, preferably two umbrella valves 631, a membrane(s) 632, a valve plate(s) 633, the cup bottom cover 634 and a glass cover 635 located at the bottom of the reaction chamber 524 within the cup body 520.

FIG. 6B shows an exploded view of the disposable test cup 300 in an alternative embodiment. The disposable test cup 300 may comprise a bottom assembly 530 including a pressure sensitive adhesive (PSA) 636 for bonding the layers together, a fluid layer 637, a compliant gasket 638, a glass cover 635 configured at the bottom of the reaction chamber 524 within the cup body 520, and a bottom cover 634. In this embodiment, the compliant gasket 638 is located at the bottom of the disposable test cup 300. Similar to the cup top 510 shown in FIG. 6A, the cup top 510 in this alternative embodiment may also comprise the cup lid 611 and a gasket 612. One or more foil seals 615 may be used to seal the parts. Alternatively, adhesive or ultrasonic bonding can be used to mate the layers together. In some aspects, the glass cover 635 may be configured directly at the bottom of the cup body 520 such as at the bottom of the reaction chamber 524, and integrated into the cup body 520 as one entity. The entire unit may be of PMMA (poly(methyl methacrylate)) (also referred to as acrylic or acrylic glass). This transparent PMMA acrylic glass may be used as an optic window for signal detection.

In some embodiments, the reaction and signal detection chamber 524 may comprise a specialized sensing area which is configured for holding a detection sensor specific for a target allergen. In some aspects, the detection sensor may be magnetic beads (e.g., polystyrene beads, and silica beads that comprise magnetite) conjugated with (SPNs) (such as aptamers and aptamer-complement complexes) that bind to the target allergen. In other aspects, the detection sensor may be a solid support (e.g., a glass surface, a chip, and a microwell) of which the surface is coated with capture probes such as SPNs (e.g., aptamers and aptamer-complement complexes) that bind to the target allergen. In some embodiments, the sensing area within the reaction and signal detection chamber 524 may be the glass cover 635 (FIG. 6A). In other aspects, the sensing area may comprise a fluidic chip (e.g., the fluidic chip 1802) including a magnetic bead collection area (e.g., a flow cell 1801 in FIGS. 18A and 18B).

Figure 18A:
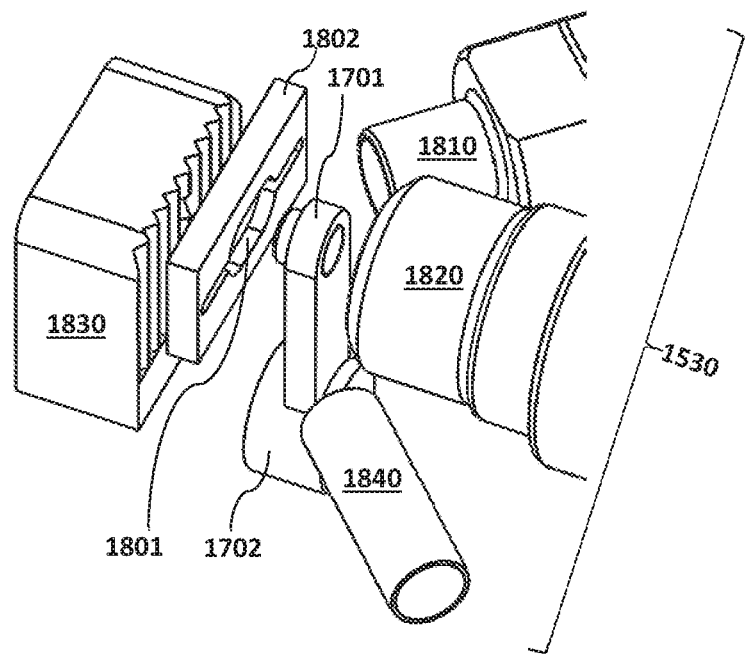
FIG. 18A is a partial perspective view of the device 100 showing the position of magnet 1701 and actuator 1702 of the magnet system 1580 when the magnet 1701 is positioned for bead collection.
Figure 18B:
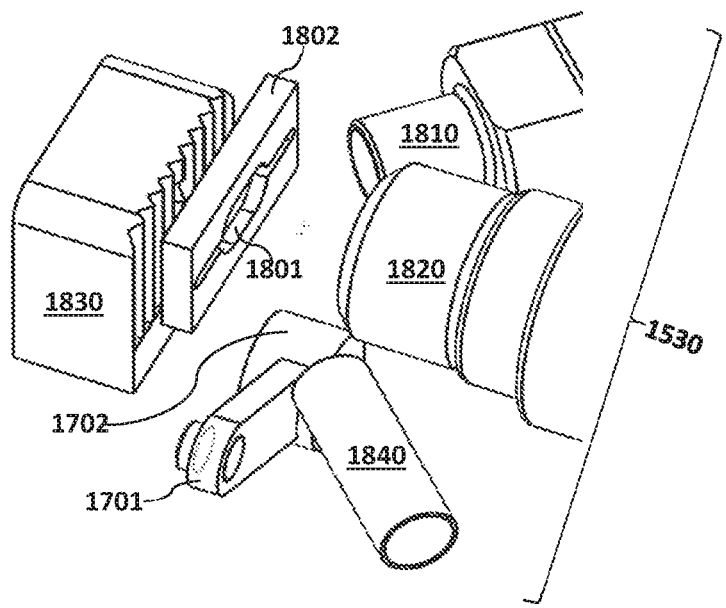
FIG. 18B is a partial perspective view of the position of magnet 1701 and actuator 1702 of the magnet system 1580 when the magnet 1701 is positioned for magnetic bead dispersal for an optical reading.
Figure 19:
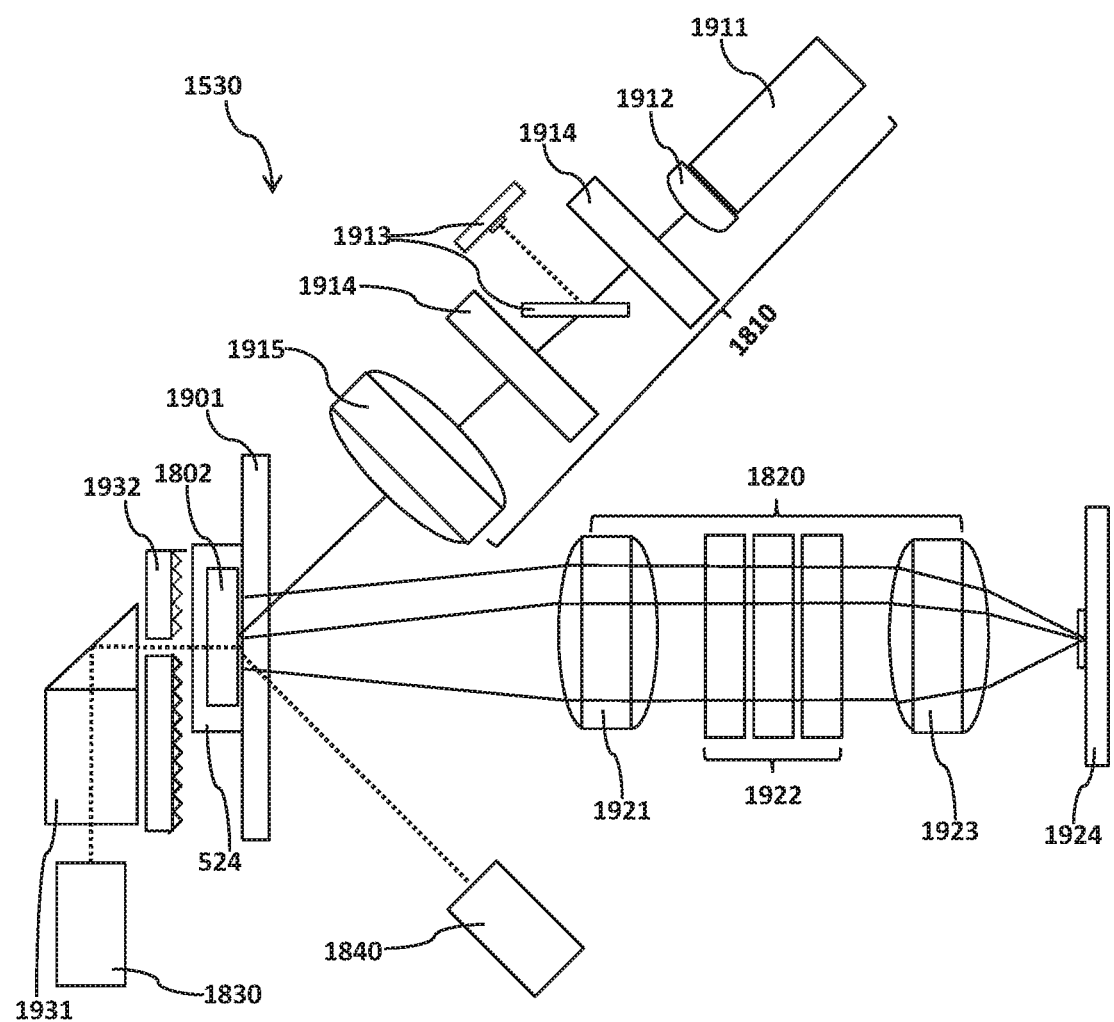
FIG. 19 illustrates an embodiment of the optical system 1530.

In some embodiments, the reaction and signal detection chamber 524 comprises at least one optical window. In one embodiment, the chamber comprises two optical windows, one primary optical window 525 and one secondary optical window 526. In one embodiment, as illustrated in FIGS. 5A and 5B, the primary optical window 525 is located at the bottom of the test cup body 520; the primary optical window 525 also serves as the interface of the reaction chamber 524 to the detection device 100, in particular to the optical system 1530 (as shown in FIGS. 15, 18A and 18B) of the detection device 100. A glass cover 635 may be inserted between the optical window and the interface of the optical system (see, e.g., FIG. 6A and FIG. 6B). The secondary optical window 526 is located at one side of the reaction chamber (FIG. 5 and FIG. 7); the secondary optical window 526 allows the absorbance light source into the reaction chamber to detect light absorption. In some aspects, the secondary optical window 526 may be constructed for reading light absorption and scattered light. In other embodiments, the reaction chamber 524 may comprise another separate optical window for reading scattered light. The optical window may be provided with a glass protective cover 1901 (as shown in FIG. 19).

Figure 7:
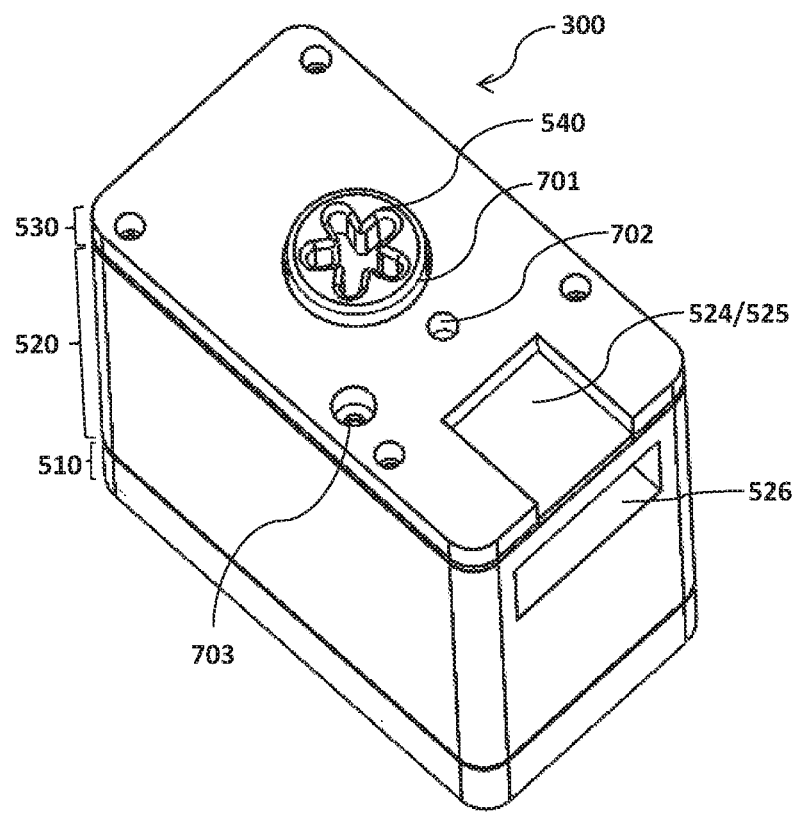
FIG. 7 is a perspective view of the bottom of the test cup 300.

The cup bottom assembly is configured for closing the disposable test cup 300 and providing means for coupling the detection device as well. As shown in FIG. 7, the bottom side of the bottom assembly 530 may include several interfaces for connecting the cup 300 to the detection device 100 for operation, including a homogenization rotor interface 701 for the homogenization rotor 540; an interface 702 for holding the pinch valve(s); and a pump interface 703 for connecting to the pump 1540 (shown in FIG. 15) in the detection device 100.

In some embodiments, the valve system configuring for controlling the fluid flow of the sample, buffer and other reagents through different parts of the cartridge is included. In addition to flexible membranes, foil seals and pinch valves discussed herein, other valves may be included to control the flow of the fluid during the process of a an allergen detection testing, including swing check valves, gate valves, ball valves, globe valves, or other commercially available valves.

Figure 8:
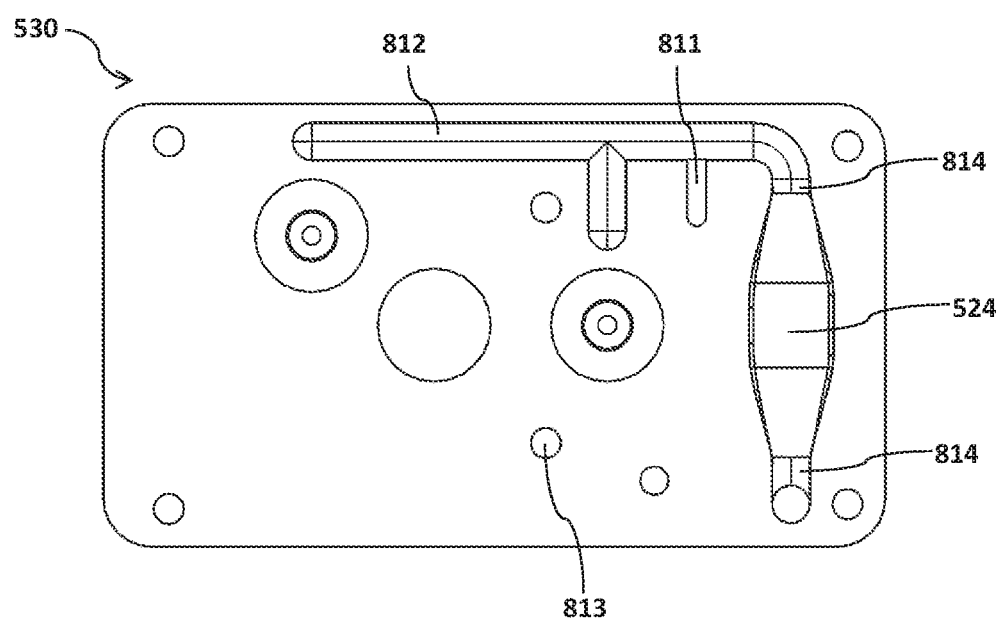
FIG. 8 illustrates the upper surface of the cup bottom 530, showing the flow channel 812, reaction and detection chamber 524 and air port 813.

In one embodiment, means for controlling the fluid flow within the cup chambers may be included in, for example, the cup bottom assembly 530. The means may comprise flow channels, tunnels, valves, gaskets and air connections. The exploded view of the cup bottom 530 in FIG. 6B demonstrates each layer including those configured for controlling the fluid flow. As further illustrated in FIG. 8, the reaction chamber 524 consists of an opening in the flow channel 812 enclosed within a solid support, i.e. a glass fluidic chip 1802 (see FIGS. 18A and 18B) coated with capture probes on the surface. The reaction chamber 524 may be completely sealed off by closing a pinch valve located at the entrance and exit sites 814 of the reaction chamber 524 (FIG. 8). The locations and numbers of pinch valve(s) at the entrance and exit sites 814 may vary. Accordingly, the locations and numbers of valve interfaces 702 at the cup bottom 530 may also vary.

The flow channel 812 at the bottom of the test cup 300 is provided for delivering the solution to the reaction chamber 524 and/or other parts within the test cup 300. An opening at both the entrance and exit sites 814 of the reaction chamber 524 is connected to the flow channel(s) 812. The opening is controlled by a pinch valve. An inlet channel air port 811 provides an interface between the test cup 300 and a positive or negative pressure source (e.g., by the pump 1540) in the detection device 100. The inlet channel air port 811 may include a gas permeable membrane to prevent fluid from leaking. In one embodiment, the inlet channel air port 811 is connected to the reaction chamber 524 through the flow channel 812.

Accordingly, the inlet channel air port 811 connects an inlet channel to atmospheric air through a gas permeable membrane. By closing the pinch valve(s) to both fluid reservoirs, air can be pulled through the gas permeable membrane into the reaction chamber to help flush food particulate from the chamber 524. The gas permeable membrane is selected such that it will only allow air into the inlet when both pinch valves are closed. Alternatively, an additional pinch valve site 814 can be used to open and close the passage to the inlet channel air port 811.

A separate air port 813 provides an interface between the test cup 300 and a positive or negative pressure source in the detection device 100. This air port 813 may be provided with a gas permeable membrane to prevent fluid from leaking. In this particular embodiment, the air port 813 is connected to the reaction chamber through the waste chamber 523.

The flowing system may be used to control the rate and direction of the processed sample solution, buffers and waste within different reservoirs such as the food processing reservoir 901, buffer storage reservoir 902 and waste reservoir 903 shown in FIG. 9 during the an allergem detection testing.

In some embodiments, one or more extraction buffers may be pre-stored in the homogenization chamber 521, for example in foil sealed reservoirs like the food processing reservoir 901 (FIG. 9). Alternatively, extraction buffers may be stored separately in a separate buffer reservoir in the cup body 520, a reservoir similar to the wash buffer storage reservoir 902 (in the buffer storage chamber 522 as shown in FIG. 5B). After sample homogenization and washing, waste may be stored in the separate waste reservoir 903 within the waste chamber 523. The waste chamber 523 has sufficient volume to store a volume greater than the amount of fluid used during the allergen detection testing.

Figure 10A:
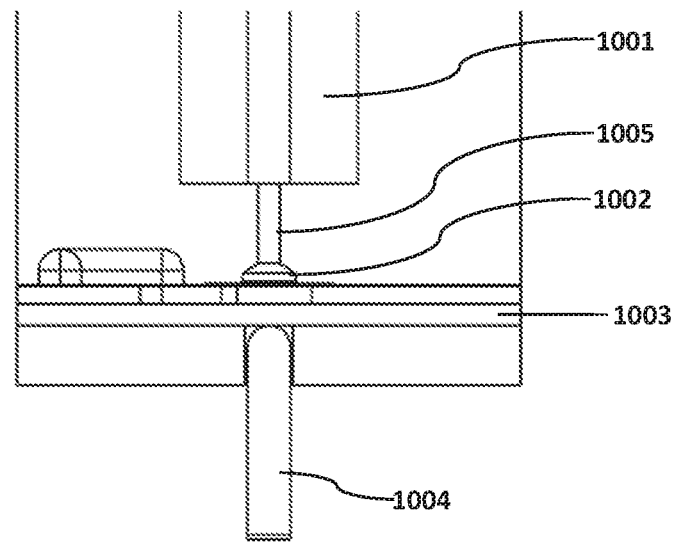
FIG. 10A illustrates a pinch valve prior to a pin 1004 breaking the foil seal 1002.
Figure 10B:
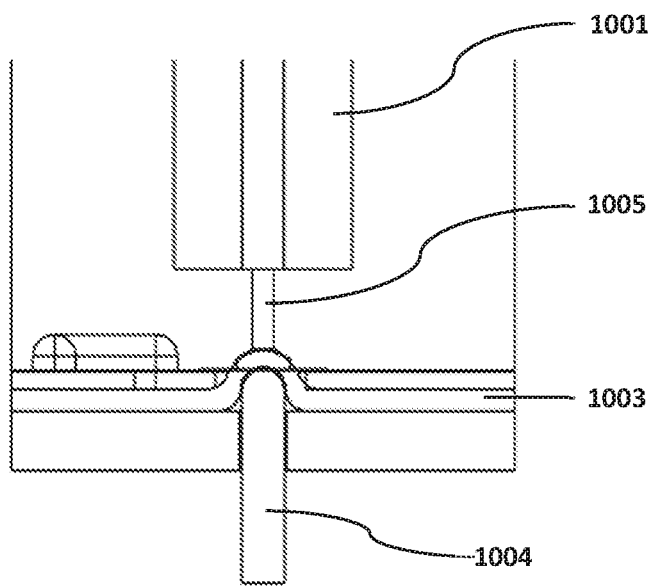
FIG. 10B illustrates the same pinch valve of FIG. 10A in the closed state, sealed by a gasket 1003 pushed upward by the pin 1004.

The pinch valve interface 702 (FIG. 7) at the bottom of the test cup comprises the foil seals 1002 that seal the fluid reservoirs 1001 which refer to the reservoirs 901, 902 and 903 as shown in FIG. 9) and the compliant gasket layer 1003 (also shown in FIG. 6B as 638). When the test cup is inserted into the detection device 100, an upwardly extending pin 1004 in the detection device will push the compliant gasket layer 1003 to a distance sufficient to puncture the foil seal 1002, thereby opening the chamber. FIG. 10A shows the relative location of the pin 1004 before it punctures the foil seal 1002. At this stage, the pinch valve is open but the buffer cannot flow from the reservoir 1001 because the foil seal 1002 prevents downward flow via the passage 1005. When the pin 1004 is pressed upward as shown in FIG. 10B, the foil seal 1002 is broken and the gasket 1003 is pushed against the opening of the passage 1005 to close the pinch valve. With subsequent downward movement of the pin 1004 after the foil seal 1002 is broken, the gasket 1003 relaxes and buffer may flow through the opening in the passage 1005. This arrangement takes advantage of gravity to induce movement of the buffer.

Figure 21:
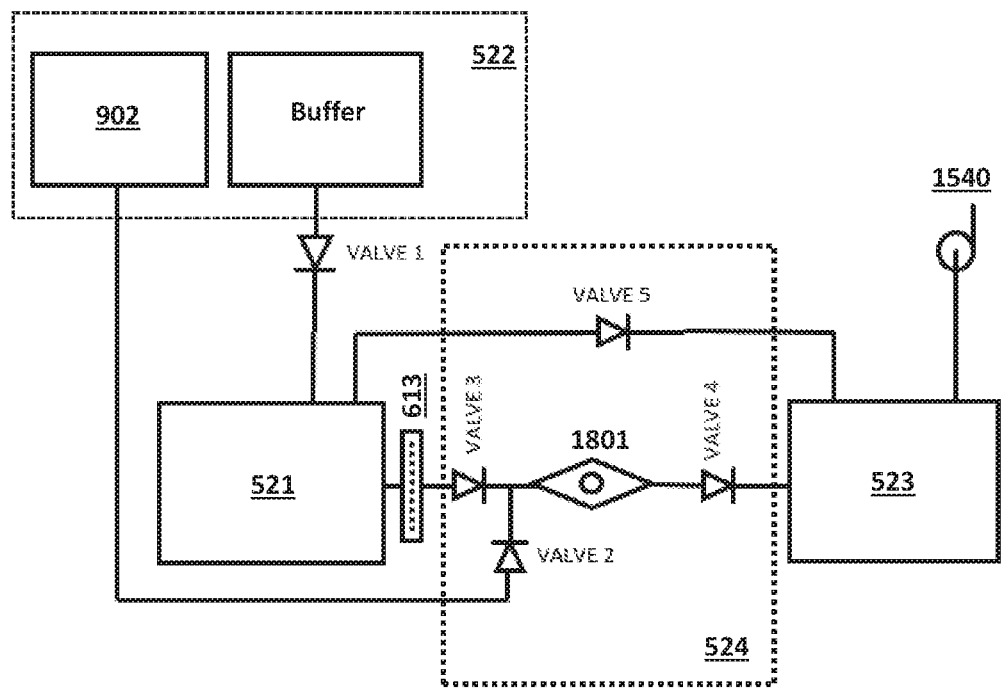
FIG. 21 is a flow chart showing a washing process for the magnetic beads and/or DNA solid plate.

Valves are provided to separate different parts/chambers inside the test cup 300, including a valve between the homogenization chamber 521 and the reaction chamber 524 (e.g., valve 3 indicated in FIG. 21), a valve between the homogenization chamber 521 and the waste chamber 523 (valve 5 indicated in FIG. 21).

In one embodiment, as illustrated in FIGS. 6A and 6B, the homogenization rotor 540 is inserted into the homogenization chamber 521 through the rotor port interface 701 (as shown in FIG. 7) at the cup bottom assembly 530. When the test cup 300 is inserted to the detection device 100, the homogenization rotor 540 is then connected to the motor 1510 (as shown in FIG. 15) through a coupling means.

Figure 11A:
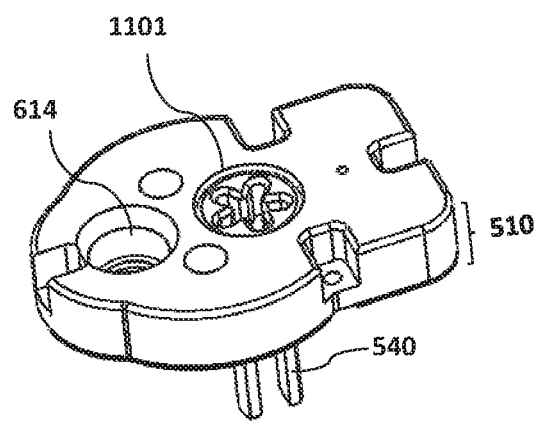
FIG. 11A illustrates an embodiment of the cup top cover 510 having a rotor port 1101.
Figure 11B:
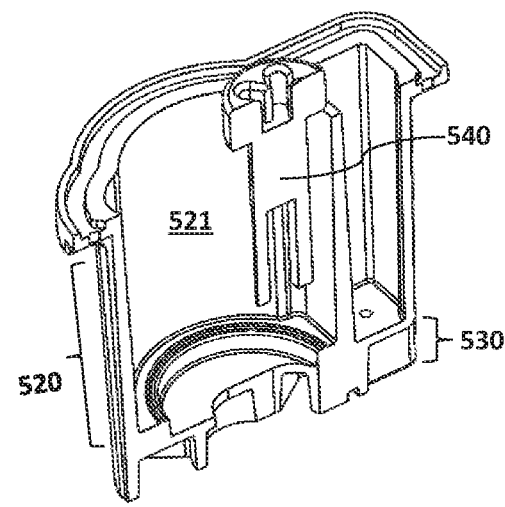
FIG. 11B (cross-sectional perspective side view) and FIG. 11C (top view) demonstrate an alternative embodiment of the homogenization rotor 540 wherein the rotor 540 is inserted into the homogenization chamber 521 through the rotor port 1101 as shown in FIG. 11A.
Figure 11C:
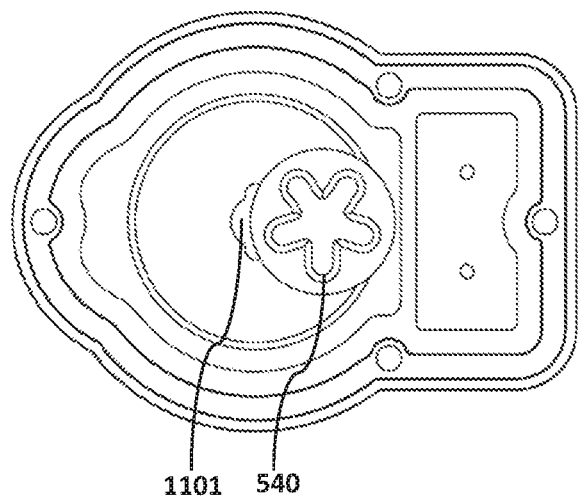

In alternative embodiments, the homogenization rotor 540 may be inserted into the homogenization chamber 521 through the rotor port 1101 on the cup top cover 510 (as shown in FIGS. 11A and 11C). This cup top cover 510, together with the cup bottom 530 and the cup body 520, then may be assembled to form a test cup 300, such as shown in FIG. 12A, FIG. 12B, FIG. 12C, FIG. 14A and FIG. 14B.

In accordance with the present invention, the homogenization rotor 540 may be constructed small enough to fit into a disposable test cup 300, particularly into the homogenization chamber 521, where the homogenizer processes a sample to be tested. Additionally, the homogenization rotor 540 may be optimized for increasing the efficacy of sample homogenization and protein extraction. In one embodiment, the homogenization rotor 540 may comprise one or more blades or the equivalent thereof at the proximal end (FIG. 6A and FIG. 6B). In some examples, the rotor 540 may comprise one, two, three or more blades. The homogenization rotor 540 is configured to pull the test sample from the food corer 200 into the bottom of the homogenization chamber 521.

Figure 12A:
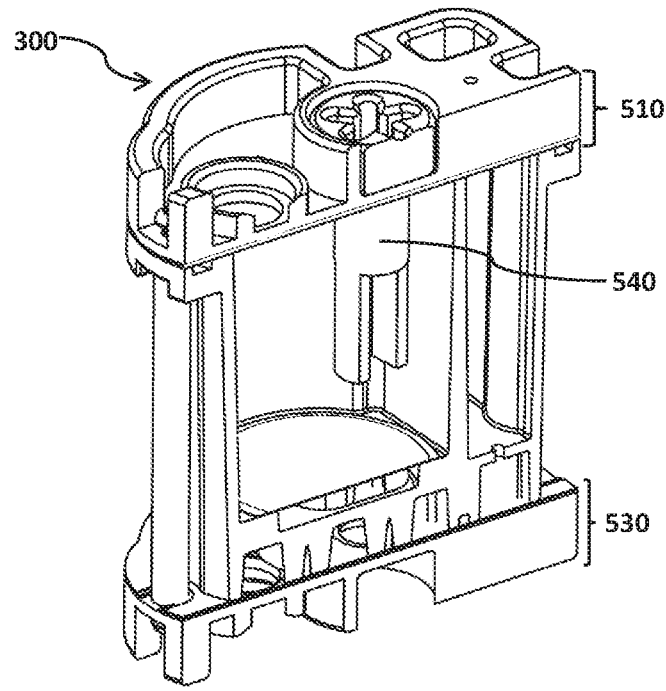
FIG. 12A to FIG. 12C show alternative embodiments of the homogenization chamber 521 and rotor 540, wherein the rotor 540 is inserted through the rotor port 1101 (as shown in FIG. 11A) on the cup top cover 510.
Figure 12B:
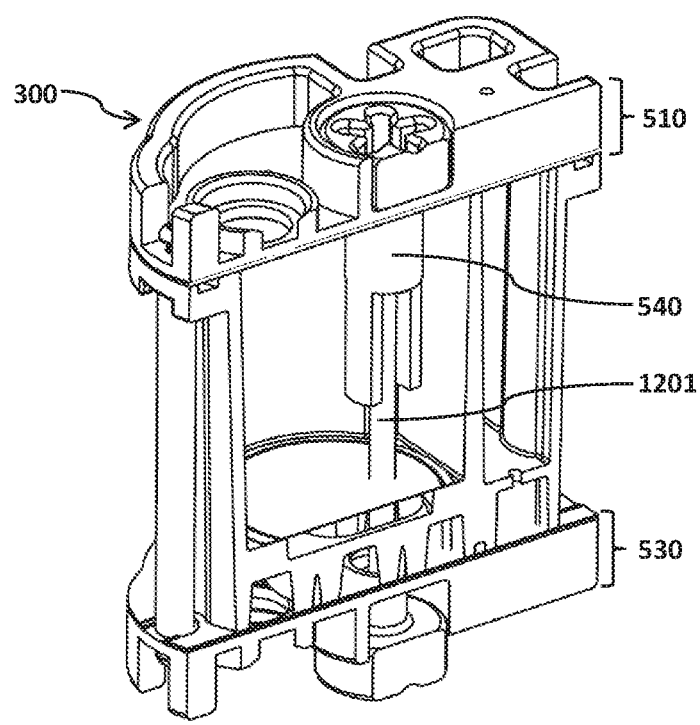
Figure 13A:
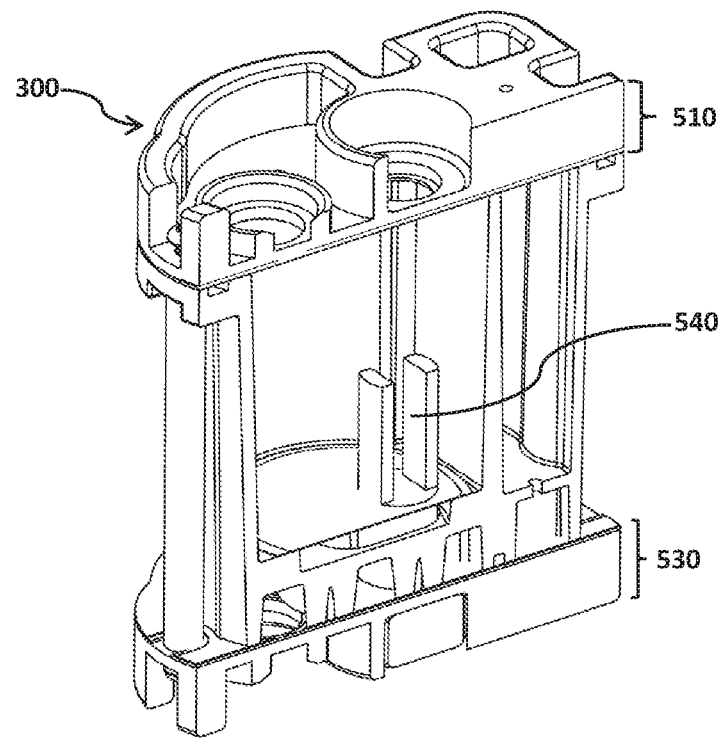
FIG. 13A to FIG. 13C show alternative embodiments of the homogenization chamber 521 and rotor 540, wherein the rotor 540 is inserted through the rotor port interface 701 (as shown in FIG. 7) at the cup bottom 530.
Figure 13B:
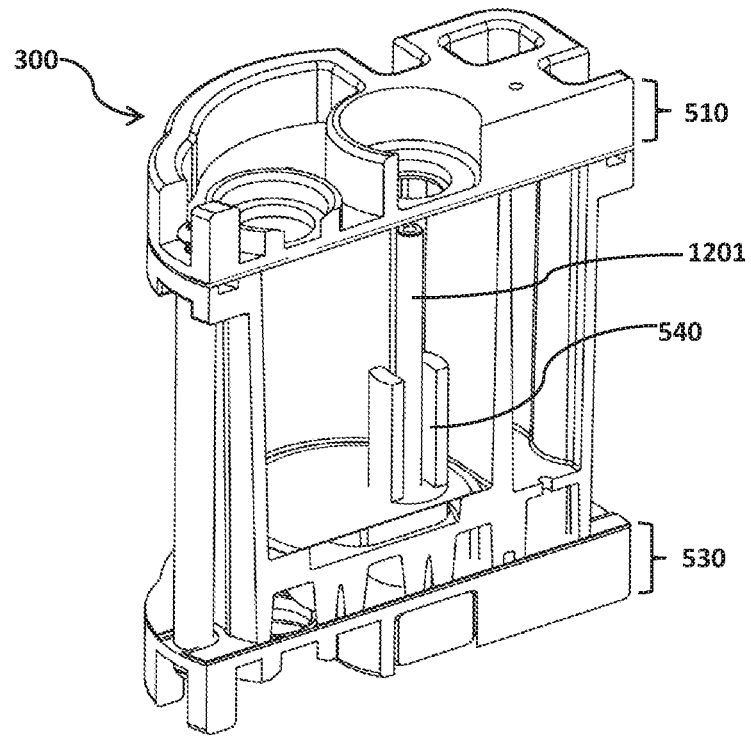

Alternatively, the homogenization rotor 540 may further comprise a center rod running through the rotor that connects through the cup body 520 to a secondary interface bit as shown in FIG. 12B and FIG. 13B. The central rod 1201 may act as an additional bearing surface or be used to deliver rotary motion to the rotor 540. When the rotor 540 is mounted to the cup body 520 through the port at the cup bottom (FIG. 12B), the blade tips may remain submersed within the extraction buffer during operation.

Figure 14A:
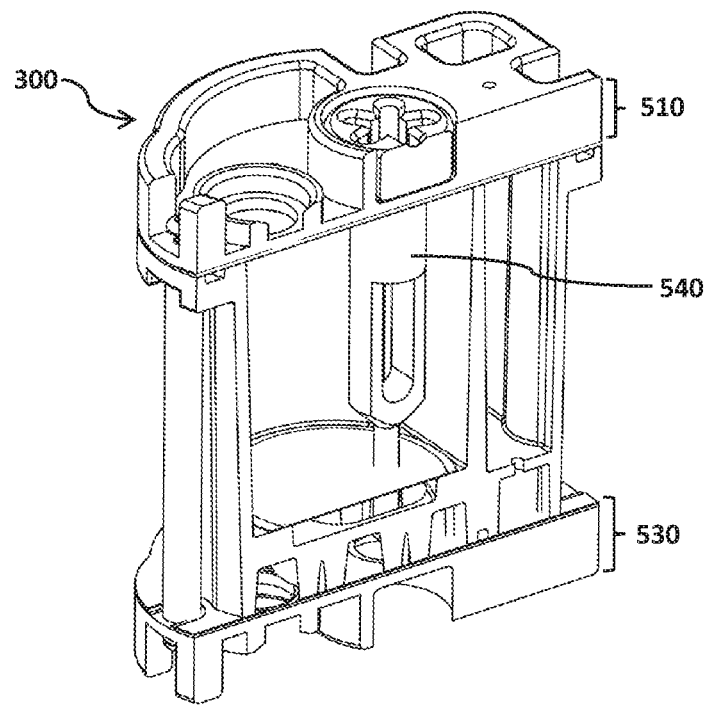
FIG. 14A and FIG. 14B show alternative embodiments of the homogenization chamber and rotor, wherein the rotor 540 is inserted through the rotor port 1101 (as shown in FIG. 11) on the cup top cover 510 and extends to the cup bottom.

In another alternative embodiment, the homogenization rotor 540 may have an extension to provide a pass through to the bottom of the cup; the pass may be used as a secondary bearing support and/or an additional location for power transmission. In this embodiment, the lower part of the rotor has a taper to fit to a shaft, forming a one piece rotor (as shown in FIG. 14A).

Figure 12C:
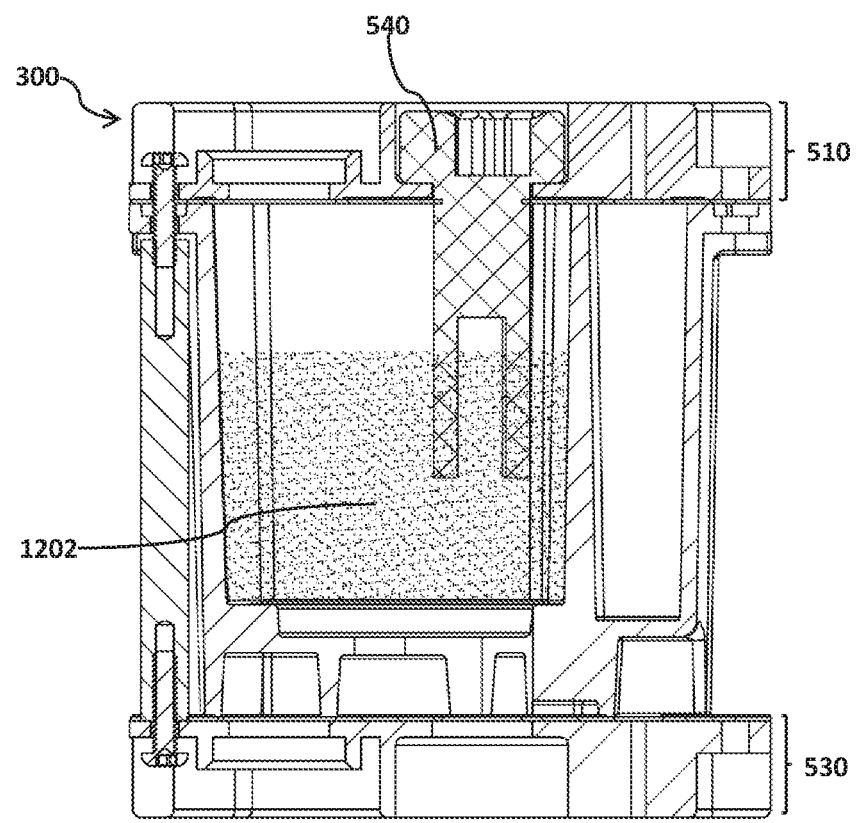
Figure 13C:
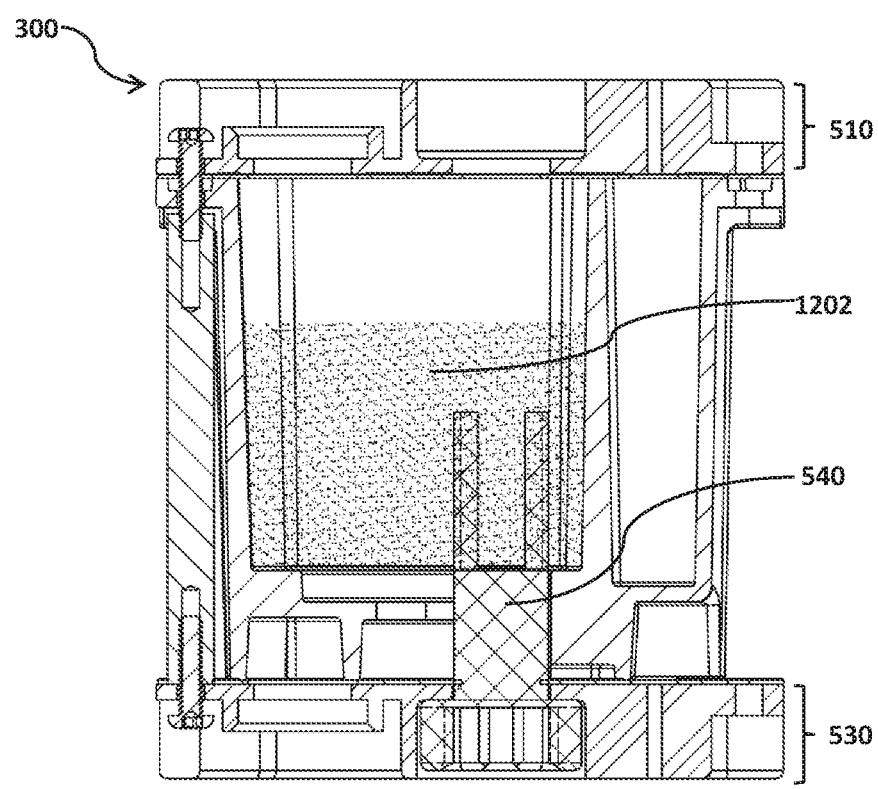
Figure 14B:
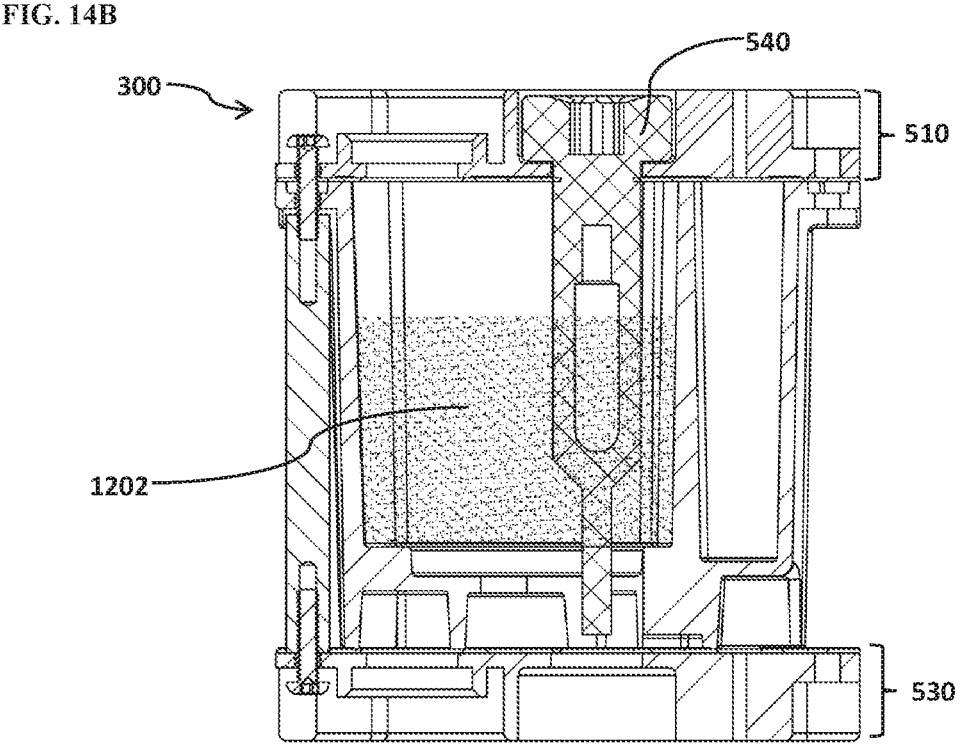

In accordance with the present invention, depth of the blades of the homogenization rotor 540, with or without the center rod, is constructed to ensure the blade tips in the fluid 1202 during sample processing (blending and/or vortexing) (as shown in FIG. 12C. FIG. 13C and FIG. 14B).

In some embodiments, the rotor 540 is offset from the center axis of the test cup 300, promoting shear against the nearside wall.

Different from other homogenizers with similar structures (e.g., U.S. Pat. No. 6,398,402; the contents of which are incorporated herein by reference in their entirety), the custom blade core of the present invention can spin and draw and force the sample into the toothed surfaces of the custom cap.

The homogenizer rotor may be made of any thermoplastics, including, but not limited to, polyamide (PA), acrylanitrilebutadienestyrene (ABS), polycarbonate (PC), high Impact Polystyrene (HIPS), and acetal (POM).

In some embodiments, the disposable cartridge (e.g., the test cup 300), may be in any shape, for example, circular, oval, rectangular or egg-shaped. Any of these shapes may be provided with a finger cut or notch. The disposable cartridge may be asymmetrical, or symmetrical.

Optionally, a label or a foil seal may be included on the top of the cup top cover 510 to provide final fluid seal and identification of the test cup 300. For example, a designation of peanut indicates that the disposable test cup 300 is used for detecting the peanut allergen in a food sample.

The Detection Device

In some embodiments, the detection device 100 may be configured to have an external housing 101 that provides support surfaces for the components of the detection device 100; and an optional small lid that opens the detection device 100 for inserting a disposable test cup 300 and covers the cup during operation. The small lid may be located at one side of the device, or in the center (not shown). In some aspects, the lid may be transparent, allowing all the operations to be visible through the lid.

Figure 16A:
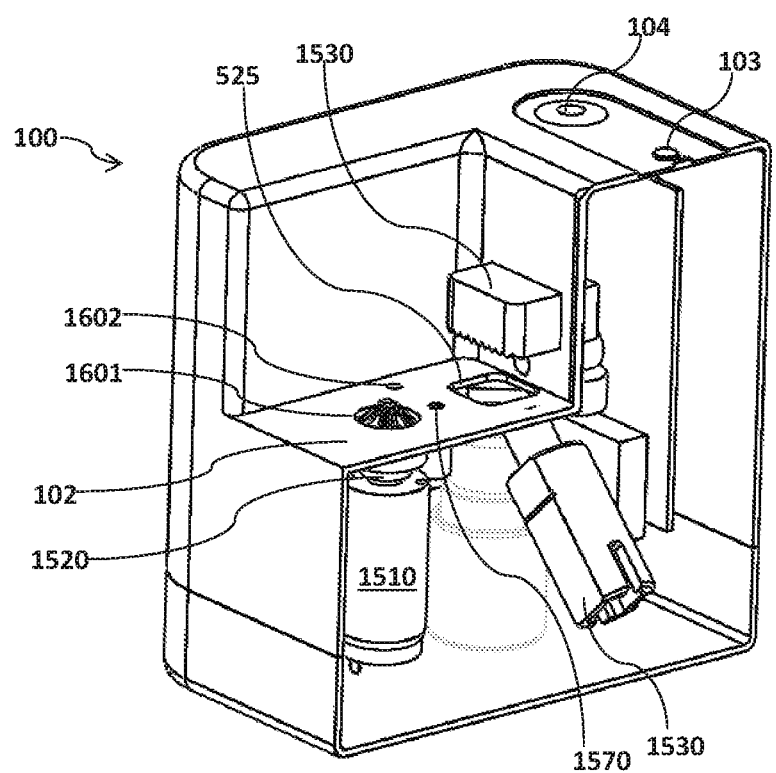
FIGS. 16A and 16B are perspective views of the primary mate plane or receptacle 102 and interfaces that connect the detection device 100 to the test cup 300.

One embodiment of the allergen detection device 100 according to the present invention is depicted in FIG. 1, FIG. 2 and FIG. 15. As illustrated in FIG. 1, the detection device 100 comprises an external housing 101 that provides support for holding the components of the detection device 100 together and integrates them as a functional integrity for implementing an allergen detection testing; the external housing 101 may be formed of plastic or other suitable support material. The device also has a mate plane or receptacle 102 for docking the test cup 300 (FIG. 1 and FIG. 16A).

Figure 16B:
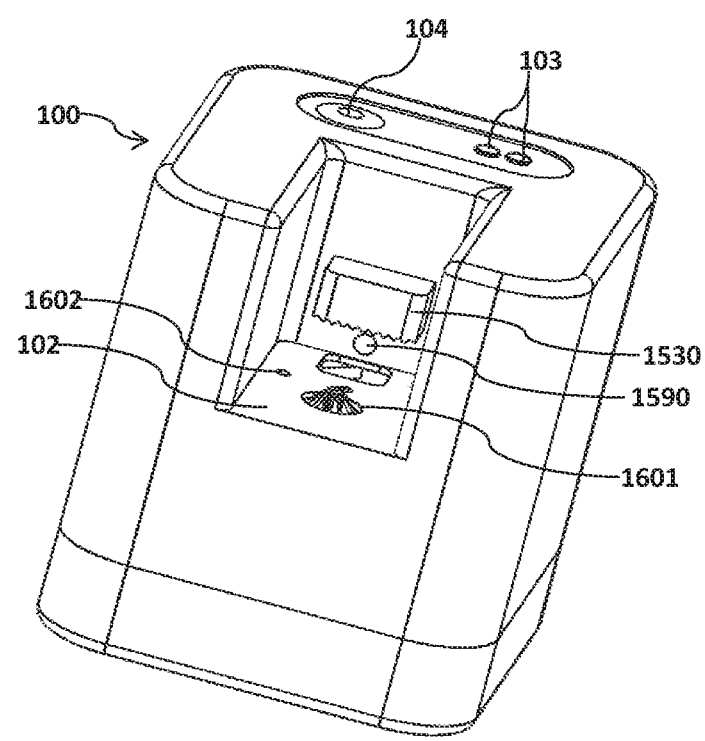

To execute an allergen detection test, the detection device 100 is provided with the following components: a homogenization assembly which is configured for homogenizing a test sample and extracting allergen proteins from the test sample in an extraction buffer; means (e.g., a motor) for operating the homogenization assembly and necessary connectors that connect the motor to the homogenization assembly; means for driving and controlling the flow of the processed sample solution during the process of the allergen detection testing; an optical system; means for detecting fluorescence signals from the detection reaction between the allergen in the test sample and the detection agents; means for visualizing the detection signals including converting and digitizing the detected signals; a user interface that displays the test results; and a power supply. In one embodiment, the homogenization assembly is connected to the homogenization rotor 540 of the test cup 300 when the test cup 300 is inserted into the detection device 100 through the mate plane or receptacle 102 that includes several interfaces for connecting the test cup 300 and the detection device 100 (FIG. 16A and FIG. 16B).

In one embodiment of the present invention, as shown in FIG. 15, the components of the detection device 100 that are integrated to provide all motion and actuation for operating an allergen detection test, include a motor 1510 which may be connected to the homogenization rotor 540 inside the homogenization chamber 521 within the cup body 520 through a multiple-component coupling assembly 1520 that may include a gear train/drive platen for driving the rotor during homogenization in an allergen detection test, an optical system 1530 that is connected to the reaction chamber 524 (not shown) of the disposable test cup 300; a pump 1540 for controlling and regulating the flow rate, a PCB 1550, a power supply 1560, a valve actuator 1570, a magnet system for bead collection 1580, and a vibratory resuspension actuator 1590.

1. Homogenization Assembly

In one embodiment, the motor 1510 may be connected with the homogenization rotor 540 inside the test cup 300 through the multiple-component rotor coupling assembly 1520 (FIG. 15 and FIG. 16A). The rotor coupling assembly 1520 may include a coupling that is directly linked to the distal end cap of the rotor 540, and a gearhead that is part of a gear train or a drive (not shown) for connection to the motor 1510. In some embodiments, the coupling may have different sizes at each end, or the same sizes at each end of the coupling. The distal end of the coupling assembly 1601 (FIG. 16A and FIG. 16B) will connect to the rotor through the rotor port interface 701 (FIG. 7) at the bottom 530 of the test cup 300. It is also within the scope of the present invention that other alternative means for connecting the motor to the homogenization rotor 540 to form a functional homogenization assembly may be used.

In some embodiments, the motor 1510 can be a commercially available motor, for example. Maxon motor systems: Maxon RE-max and/or Maxon A-max (Maxon Motor ag, San Mateo. Calif., USA).

Optionally, a heating system (e.g. resistance heating, or Peltier heaters) may be provided to increase the temperature of homogenization, therefore to increase the effectiveness of sample dissociation and shorten the processing time. The temperature may be increased to between 60° C. to 95° C., but below 95° C. Increased temperature may also facilitate the binding between detection molecules and the allergen being detected. Optionally a fan or Peltier cooler may be provided to bring the temperature down quickly after implementing the test.

The motor 1510 drives the homogenization assembly to homogenize the test sample in the extraction buffer and dissociate/extract allergen proteins. The processed sample solution may be pumped or pressed through the flow tubes to the next chamber for analysis, for example, to the reaction chamber 524, in which the processed sample solution is mixed with the pre-loaded detection molecules (e.g., aptamer-magnetic bead conjugates) for the allergen detection testing.

2. Filtration

In some embodiments, means for further filtering the processed test sample may be included in the detection device. The food sample will be pressed through a filter membrane or a filtering assembly before the extraction solution being delivered to the reaction chamber 524, and/or other chambers for further processing such as washing. One example is the filter membrane(s) 613 illustrated in FIG. 6A. The membrane(s) 613 provides filtration of specific particles from the processed protein solution.

The filter membrane 613 may be a nylon, PES (polyethersulfone), Porex™, or membrane polymers such as mixed cellulose esters (MCE), cellulose acetate, PTFE, polycarbonate, PCTE (Polycarbonate) or PVDF (polyvinylidene difluoride), or the like. It may be a thin membrane (e.g., 150 µm thick) with high porosity. In some aspects, the pore size of the filter membrane 613 may range from 0.2 µm to 600 µm, or from 0.2 µm to 50 µm, or from 20 µm to 100 µm, or from 20 µm to 300 µm, or 100 µm to 600 µm or any size in between. For example, the pore size may be 0.2 µm, 1 µm, 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm 100 µm, 150 µm, 200 µm, 250 µm, 300 µm, 350 µm, 400 µm, 450 µm, 500 µm, 550 µm, or 600 µm.

In some aspects, filter membranes may be used in combination to filter specific particles from the sample for analysis. This filter membrane may include multistage filters. Filter membranes and/or filter assemblies may be in any configuration relative to the flow valve. For example, the flow valves may be above, below or in between any of the stages of the filtration.

3. Pump and Fluid Motion

In accordance with the present invention, a means for driving and controlling the flow of the processed sample solution is provided. In some embodiments, the means may be a vacuum system or an external pressure. As a non-limiting example, the means may be a multifunctional platen (e.g., a welded plastic clamshell) which supports the axis of the gear train and it could provide the pumping (sealed air channel) for the vacuum to be applied from the pump 1540 to the test cup 300. The pump 1540 (shown in FIG. 15) may be connected to the test cup 300 through the pump port 1602 (FIG. 16A) located in the mate plane 102 of the detection device 100, which connects to the pump interface 703 (FIG. 7) on the bottom 530 of the test cup 300 when the cup is inserted to the device.

The pump 1540, such as a piezoelectric micro pump (Takasago Electric, Inc., Nagoya, Japan) may be used to control and automatically adjust the flow to a target flow rate. The flow rate of the pump is adjustable by changing either the driver voltage or drive frequency. The pump 1540 shown in FIG. 15 is a representation of piezo pumps currently on the market that have specifications suitable for the aliquot function required to flow filtered sample solution to different chambers inside the test cup 300. The pump 1540 may be a vacuum pump or another small pump designed for laboratory use such as a KBF pump (KNF Neuberger, Trenton, N.J., USA).

Alternatively, a syringe pump, diaphragm and/or a micro-peristaltic pump may be used to control fluid motion during the process of an allergen detection test and/or supporting fluidics. In one example, an air operated diaphragm pump may be used.

4. Magnet and Actuators

In some embodiments of the present invention, several actuators are provided to manipulate the samples and agents during an allergen detection test, for example, for washing the solid surface and/or magnetic beads, and/or collection and re-suspension of magnetic beads.

Figure 17:
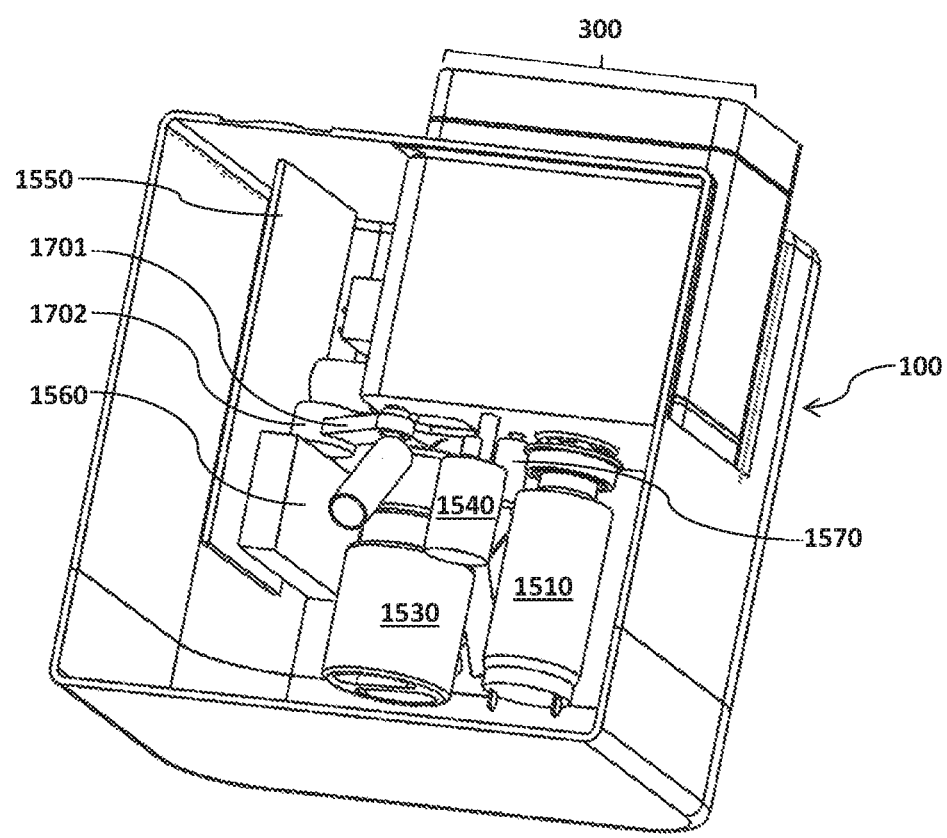
FIG. 17 is a perspective view of an optical read state of the detection device 100.

In some embodiments, the magnet system 1580 configured for magnetic bead collection (FIG. 15) may comprise a magnet 1701 and a magnet actuator 1702 as shown in FIG. 17 in the detection device 100, providing a magnetic force to keep/retain the magnetic particles in a specific sensing area within the reaction chamber 524, for example, a flow cell (1801 in FIG. 18) in the reaction chamber 524. FIG. 17 demonstrates the position of the magnet 1701 and the magnet actuator 1702 at a state for obtaining an optical reading with the magnet 1701 pointing away from the reaction chamber 524. In this state, the actuator 1702 is out of the field of view, while in the bead collection state, magnet 1701 is directly in the optical path in line with the reaction chamber 524. The magnet system for magnetic bead collection 1580 may be aligned with the bottom (i.e. the optical window 525) of the reaction chamber 524 of the test cup 300. As discussed previously, the magnetic beads may be located in the bead collection area (e.g., the flow cell 1801 as shown in FIG. 18) in the fluidic chip 1802 which can be inserted to the reaction chamber 524. In some embodiments, the glass cover 635, for example, the PMMA acrylic glass integrated with the cup chamber 524 may serve as a bead collection area. As further illustrated in FIG. 18A, the magnet 1701 can be moved into the face of the fluidic chip 1802 or the glass cover 635 by the magnet actuator 1702 to collect the magnetic beads and retain the beads in the collection area (the flow cell 1801). In the optical read state, as shown in FIG. 18B, the magnet 1701 is moved away from the fluidic chip 1802 or the glass cover 635, allowing the bead collection area to be in the axial field of view of the optical path.

In some embodiments, the magnet 1701 may be a permanent magnet or an electromagnet. The actuator 1702 is adapted to apply a magnetic field to the detection area (e.g., the flow cell 1801) of sufficient strength to direct magnetic beads to the detection area and to retain them during washing. In some aspects, a single magnet 1701 or a plurality of magnets arranged in the actuator 1702 such that a magnetic field is created that is strong enough to collect all magnetic beads may be used.

In some embodiments, in addition to the magnet system 1580 configured to collect magnetic beads for optical analysis, a second magnet system may be included for collecting magnetic beads during the washing process.

In accordance with the present invention, the magnet system(s) aims to concentrate magnetic beads and expose the beads to wash buffer and fluid sample with minimal bead aggregation, thereby increasing the interaction between detection agents conjugated to the beads and the fluid sample.

A vibratory resuspension actuator 1590 is included for facilitating the resuspension of the magnetic beads in wash buffer or in the processed sample solution (FIG. 15). The actuator 1590 can sonicate/agitate the cup to increase the mixing of magnetic particles with buffers or the fluid sample. In some embodiments, vibratory magnetic particle resuspension may be ultrasonic, simple low frequency vibration through direct or indirect contact with the reaction chamber 524. In other embodiments, the magnet and actuator 1580 of the magnetic collection system may also be used to move magnetic beads, together with the vibratory resuspension actuator 1590, to aid in resuspension. The vibratory resuspension actuator 1590, when the test cup 300 is inserted in to the detection device, may be either under the bottom of the test cup or on the side of the test cup.

In one embodiment, the actuator 1590 may be an ultrasonic wave generator which serves as the actuator for carrying out an ultrasonic process of re-suspending the magnetic beads. As a non-limiting example, an ultrasonic horn may be provided performing an ultrasonic process to blend the magnetic beads in the processed sample. The shape and other attributes of the ultrasonic horn serving as the ultrasonic wave generator are not prescribed in particular. The ultrasonic horn may have any features including the shape, as long as the ultrasonic-wave is capable of carrying out an ultrasonic process in accordance with the allergen detection method provided by the present disclosure. It is also possible to make use of an ultrasonic probe or the like in place of the ultrasonic horn. The ultrasonic horn can be constructed properly into any configuration as long as the configuration allows the process to be carried out on the beads.

A valve actuator 1570 (as shown in FIG. 15 and FIG. 17) may be included to operate the valves between different parts or chambers in the test cup 300, such as a valve between the homogenization chamber 521 and the reaction chamber 524 (FIG. 21).

5. Optical System

The detection device 100 of the present invention comprises an optical system that detects optical signals (e.g., a fluorescence signal) generated from the interaction between an allergen(s) in the sample and detection agents (e.g., aptamers or aptamer-complement complexes). The optical system may comprise different components and variable configurations depending on the types of fluorescence signal to be detected. The optical system is close and aligned with the detection cartridge, for instance, the primary optical window 525 and the secondary optical window 526 of the reaction chamber 524 of the test cup 300 as discussed above (FIG. 7).

In some embodiments, the optical system 1530 may include excitation optics 1810, emission optics 1820, absorption optics 1830, and scatter optics 1840 (FIGS. 18A and 18B).

In some embodiments, the excitation optics 1810 may comprise a light source 1911 configured to transmit an excitation optical signal to the sensing area (e.g. the magnetic bead collection area on the fluidic chip 1802 or the glass cover 635) in the reaction chamber 524, a lens 1912 configured to focus the light from the light source, at least one excitation filter(s) 1914 and an optional LED power monitoring photodiode 1913 and a focus lens 1915 (FIG. 19).

A light source 1911 is arranged to transmit excitation light within the excitation wavelength range. Suitable light sources include, without limitation, lasers, semi-conductor lasers, light emitting diodes (LEDs), and organic LEDs. An optical lens 1912 may be used along with the light source 1911 to provide excitation source light to a fluorophore. An optical filter or filters 1914 may be used to limit the range of excitation light wavelengths. In some aspects, the filter may be a band-pass filter.

Figure 22A:
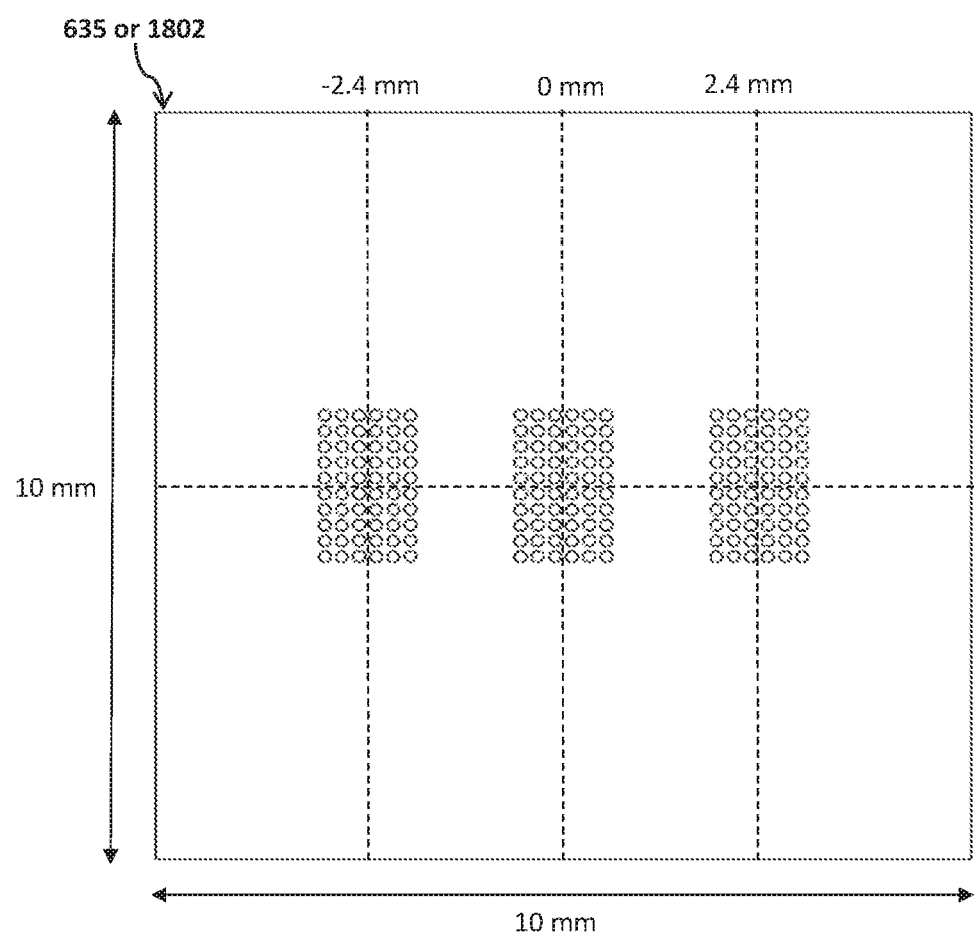
FIG. 22A is a diagram displaying the test area and control areas on a chip sensor (e.g., 635 or 1802).

Fluorescently labeled aptamers specific to a target allergen at the magnetic bead collection area (e.g., the flow cell 1801 as shown in FIG. 18), or on the solid surface (e.g., a glass chip as shown in FIG. 22A), are capable of emitting, in response to excitation light in at least one excitation wavelength range, an allergen-binding dependent optical signal (e.g. fluorescence) in at least one emission wavelength range.

In some embodiments, the optical system comprises the emission optics 1820 operable to collect emissions upon the interaction between detection agents and target allergens in the test sample from the reaction chamber 524. The emission optics 1820 may comprise a collection lens 1921 configured to collect light emitted from the reaction chamber 524, emission filters 1922, a focus lens 1923 configured to focus at least one portion of the allergen-dependent optical signal onto the detector (photodiode) 1924, and a detector (e.g., photodiode) 1924 configured to detect an allergen-dependent optical signal emitted from the sensing area (e.g. the magnetic bead collection area on the fluidic chip 1802, or nucleic acid (e.g., SPN) coated glass 635) in the reaction chamber 524 (FIG. 19).

In some aspects, more than one emission optical system 1820 may be included in the detection device. As a non-limiting example, three photodiode optical systems may be provided to read fluorescence signals from an unknown test area and two control areas on a glass chip (e.g., see FIGS. 22A and 22B).

Emission filters (such as dichroic filters or other filters) 1922 can filter the emitted light from the reaction chamber 524, allowing substantially only light with wavelengths in the emission band to reach the detector 1924 for measuring the optical signals. For example, a fluorophore dye Alexa Fluor 647 which is used to label aptamers specific for binding to a target allergen is responsive to excitation light (absorption) in the range of about 600 to 650 nm (absorption peak 647 nm) and can emit light within an emission wavelength range of about 670 to 750 nm with an emission peak of about 680 nm. Thus in one embodiment, the detection agents include Alexa Fluor 647, and the detectors 1924 can be filtered from light having a wavelength shorter than about 650 nm or shorter than about 670 nm.

A detector (e.g., photodiode) 1924 is arranged to detect light emitted from the fluidic chip in the emission wavelength range. Suitable detectors include, without limitation, photodiodes, complementary metal-oxide-semiconductor (CMOS) detectors, photomultiplier tubes (PMT), microchannel plate detectors, quantum dot photoconductors, phototransistors, photoresistors, active-pixel sensors (APSs), gaseous ionization detectors, or charge-coupled device (CCD) detectors. In some aspects, a single and/or universal detector can be used.

In some embodiments, the optical system 1530, through the absorption optics 1830, may also illuminate the magnetic beads or a chip (e.g. glass cover 635) within the detection/reaction chamber 524 with light having wavelengths in an absorption band to detect absorption. The absorption optical path may include waveguide 1931 and beam dump 1932 (FIG. 19).

In some embodiments, the optical system 1530 further comprises scatter optics 1840 to measure light that is scattered by the magnetic beads, the sample and/or other surfaces during the process of an allergen detection testing.

In accordance with the present invention, the parts of the optical system are configured to perform three detection modes: fluorescence signal, scatter light signal and light absorption. Changes in the scattering and absorption of light in the reaction chamber 524 such as reflectance, are monitored and recorded (FIG. 20B and FIG. 20C).

A scatter mode of optics may be used to determine whether a food sample is transferred into the reaction chamber 524. As shown in FIG. 20B, light incident on magnetic collecting area on the fluid chip 1802 (or the glass cover 635) (within the reaction chamber 524) is scattered by the display in all directions. A portion of the light that is scattered in the scatter mode enters the optical system. In one embodiment, the scattered signal read may be used as a reference optical signal for normalizing the primary allergen dependent fluorescence reading (FIG. 20A) for scattering of light emitted from the sensing area. Accordingly, at least one corrected signal value may be calculated in dependence upon the measured scattered light read.

Figure 20C:
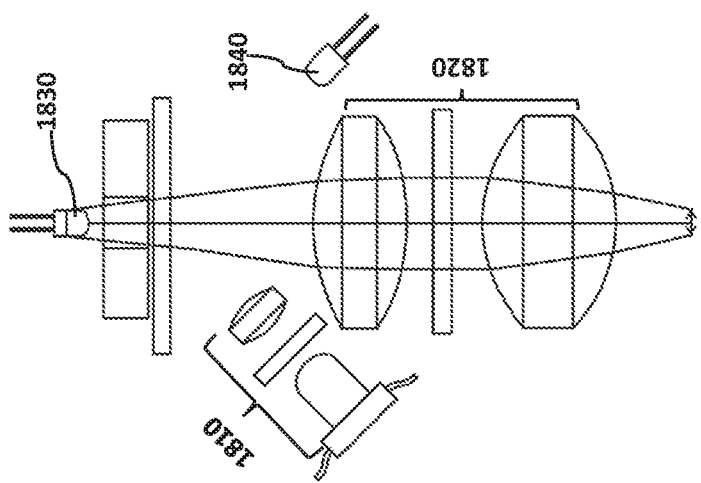
FIG. 20A to FIG. 20C illustrate three optical modes.
Figure 20B:
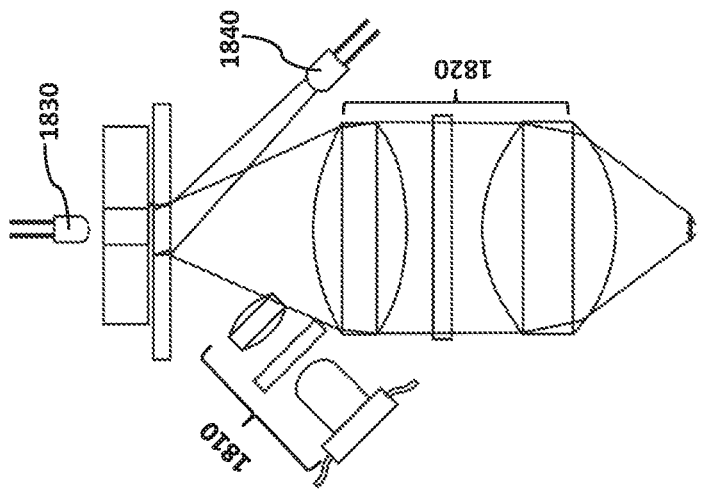
Figure 20A:
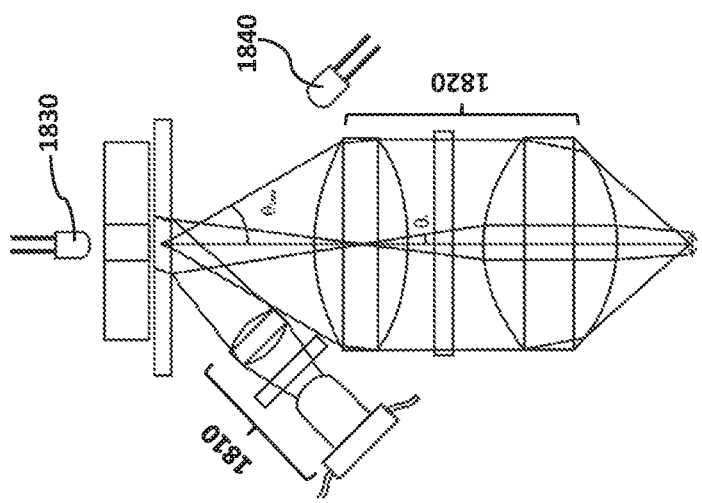

In some embodiments, prior to measuring optical reads for the allergen dependent fluorescence signal (FIG. 20A) and the scattered optical signal (FIG. 20B), an absorption reading may be taken to measure the background and light absorbed by the substances, such as magnetic beads (FIG. 20C). This reading may be used to further correct the signals, e.g., by background subtraction. An allergen value then is determined from an allergen dependent optical signal and/or a ratio of multiple optical signals including one or more reference signals.

The above described optical system 1530 is an illustrative example of certain embodiments. In some embodiments, the optical system will have different configurations and/or different components.

In other embodiments, a computer or other digital control system can be used to communicate with the light filters, the fluorescence detector, absorption detector and scatter detector. The computer or other digital control systems control the light filter to subsequently illuminate the sample with each of the plurality of wavelengths while measuring absorption and fluorescence of the sample based on signals received from the fluorescence and absorption detectors.

6. Display

As shown in FIG. 15, a printed circuit board (PCB) 1550 is connected to the optical system 1530. The PCB 1550 may be configured to be compact with the size of the detection device 100 and at the same time, may provide enough space to display the testing result.

In accordance, the test result may be displayed with back lit icons, LEDs or an LCD screen, OLED, segmented display or on an attached mobile phone application. The user may see an indicator that the sample is being processed, that the sample was processed completely (total protein indictor) and the results of the test. The user may also be able to view the status of the battery and what kind of cartridge he/she placed in the device (bar code on the cartridge or LED assembly). The results of the test will be displayed, for example, as (1) actual number ppm or mg, or (2) binary result yes/no; or (3) risk analysis—high/medium/low or high/low, risk of presence; or (4) range of ppm less than 1/1-10 ppm/more than 10 ppm; or (5) range of mg less than 1 mg/between 1-10 mg/more than 10 mg. The result might also be displayed as number, colors, icons and/or letters.

In accordance with the present invention, the detection device 100 may also include other features such as means for providing power supply and means for providing a control of the process. In some embodiments, one or more switches are provided to connect the motor, the micropump and/or the gear train or the drive to the power supply. The switches may be simple microswitches that can turn the detection device on and off by connecting and disconnecting the battery.

The power supply 1560 may be a Li-ion AA format battery or any commercially available batteries that are suitable for supporting small medical devices such as Rhino 610 battery, Tumtigy Nanotech High dischargeable Li Po battery, or a Pentax D-L163 battery.

In the description herein, it is understood that all recited connections between components can be direct operative connections or indirectly operative connections.

Allergen Detection

In another aspect of the present invention, there is provided an allergen detection testing assay implemented using the present detection systems and devices. In some embodiments, the detection agents comprise aptamers conjugated to a solid surface such as magnetic beads or glass.

In some embodiments, the allergen detection testing assay comprises the steps of (a) obtaining a test sample suspected of containing an allergen(s) of interest, (b) homogenizing the obtained sample and extracting allergen proteins using an extraction buffer, (c) bringing a contact of the processed sample with a detection sensor which comprises magnetic beads or solid surfaces coated with aptamers and/or aptamer-complement complexes that specifically bind to a target allergen; (d) determining a fluorescence signal from the contact in (c); and (e) processing and digitizing the detected signals and visualizing the interaction between the detection agents and the allergen(s). In some aspects, the assay further comprises a step of washing and re-suspending the magnetic beads when they are used as the sensors for detecting the target allergen.

Sampling

To provide a reliable and sensitive result from an allergen detection testing, an appropriately sized sample is important. The inventors of the present invention developed a sampling mechanism that can collect a test sample effectively and non-destructively for fast and efficient extraction of allergen proteins for detection.

A sized portion of the test sample can be collected using, for example, a food corer 200 illustrated in FIG. 3B. The food corer 200 collects an appropriately sized sample which can provide enough protein extraction for the detection testing. The sized portion may range from 0.1 g to 1 g food sample, preferably 0.5 g food sample. Furthermore, the food corer 200 may pre-process the collected test sample by cutting, grinding, blending, abrading and/or filtering. Preprocessed test sample will be introduced into the homogenization chamber 521 for processing and allergen protein extraction.

The collected test sample is processed in an extraction buffer. In some aspects, an extraction buffer is present in the homogenization chamber 521 and may be mixed with the test sample by the homogenization rotor 540. In other aspects, the extraction buffer may be released into the homogenization chamber 521 from another separate storage chamber. The test sample and the extraction buffer will be mixed together by the homogenization rotor 540 and the sample being homogenized.

The extraction buffer may be a universal target extraction buffer that can retrieve enough target proteins from any test sample and be optimized for maximizing protein extraction. In some embodiments, the formulation of the universal protein extraction buffer can extract the protein at room temperature and in minimal time (less than 1 min). The same buffer may be used during food sampling, homogenization and filtering. The extraction buffer may be a PBS based buffer containing 10%, 20% or 40% ethanol, or a Tris based buffer containing Tris base pH 8.0, 5 mM MEDTA and 20% ethanol, or a modified PBS or Tris buffer. In some examples, the buffer may be a HEPES based buffer. Some examples of modified PBS buffers may include: P+ buffer and K buffer. Some examples of Tris based buffers may include Buffer A+, Buffer A, B, C, D, E, and Buffer T. In some embodiments, the extraction buffer may be optimized for increasing protein extraction. A detailed description of each modified buffer is disclosed in the PCT Patent Application No.: PCT/US2014/062656; the content of which is incorporated herein by reference in its entirety.

The volume of the extraction buffer may be from 0.5 mL to 3.0 mL. In some embodiments, the volume of the extraction buffer may be 0.5 mL, 1.0 mL, 1.5 mL, 2.0 mL, 2.5 mL or 3.0 mL. These volumes provide efficient and repeatable results over time and in different food matrices.

In accordance with the present invention, the test sample is homogenized and processed using the homogenization assembly that has been optimized with high speed homogenization for maximally processing the test sample. In some aspects, a filtering mechanism may be linked to the homogenizer. The homogenized sample solution is then driven to flow through a filter processing to further extract allergen proteins, lowering the amount of other molecules extracted from the test sample. A filter membrane such as cell strainer from CORNING (CORNING, N.Y., USA) or similar custom embodiment may be connected to the homogenizer. The filtering process may be a multi-stage arrangement with changing pore sizes from first filter to second.

In some aspects, the sampling procedure provides effective protein extraction in less than 1 minute. In one aspect, speed of digestion may be less than 2 minutes including food sampling, digestion and readout. Approximately, the procedure may last 15 seconds, 30 seconds, 45 seconds, 50 seconds, 55 seconds or 1 minute.

Sensors and Detection Agents

Extracted allergen proteins may be mixed with one or more detection agents that are specific to one or more allergens of interest. The interaction between allergen protein extraction and detection agents will generate a detectable signal which indicates the presence, or absence or the amount of one or more allergens in the test sample. As used herein, the term "detection agent" or "allergen detection agent" refers to any molecule which interacts with and/or binds to one or more allergens in a way that allows detection of such allergen in a sample. In one aspect of the present invention, the detection agents are nucleic acid molecule based signaling polynucleotides (SPNs), such as aptamers or aptamer-complement complexes.

In accordance with the present invention, the sensors may comprise detection agents composed of nucleic acid molecules and magnetic beads. The magnetic beads are conjugated with aptamers and/or aptamer-complement complexes. The DNA-magnetic bead conjugates mayx be provided as lyophilized powder or in aqueous solution. The beads may be preloaded to the sensing area within the reaction chamber 524 (e.g., the flow cell 1801) (FIGS. 18A and 18B).

In other embodiments, the sensor may be a solid substrate coated with SPNs, aptamers and/or aptamer-complement complexes that specifically bind to a target allergen, for example, the glass cover 635 inserted into the reaction chamber 524 of the present invention. The sensor may also be a separate glass chip, a microwell, an acrylic glass, or a microchip, of which the surface is coated with allergen specific SPNs, aptamers and/or aptamer-complement complexes. As used herein, the term "aptamer" refers to a nucleic acid species that has been engineered through repeated rounds of in vitro selection or equivalently, SELEX (systematic evolution of ligands by exponential enrichment) to bind to various molecular targets such as small molecules, proteins, nucleic acids, and even cells, tissues and organisms. The binding specificity and high affinity to target molecules, the sensitivity and reproducibility at ambient temperature, the relatively low production cost, and the possibility to develop an aptamer core sequence that can recognize any protein, ensure an effective yet simple detection assay for the sensors of the detection device as described herein.

In accordance with the present invention, aptamer molecules that can be used as detection agents may be aptamers specific to a common allergen such as peanut, tree-nut, fish, gluten, milk and egg. For example, the detection agent may be the aptamers or aptamer-complement complexes described in applicants' relevant U.S. Provisional Application Ser. Nos. 62/418,984, filed on Nov. 8, 2016; 62/435,106, filed on Dec. 16, 2016; and 62/512,299 filed on May 30, 2017; and the PCT application No. PCT/US2017/060487 filed on Nov. 8, 2017; which are commonly owned and incorporated herein by reference in their entirety.

In some embodiments, the detection agent may be labeled with a fluorescence marker. The fluorescence marker or fluorophore may suitably have an excitation maximum in the range of 200 to 700 nm, while the emission maximum may be in the range of 300 to 800 nm. The fluorophore may further have a fluorescence relaxation time in the range of 1-7 nanoseconds, preferably 3-5 nanoseconds. As non-limiting examples, a fluorophore that can be probed at one terminus of a SPN may include derivatives of boron-dipyrromethene (BODIPY e.g., BODIPY TMR dye; BODIPY FL dye), Fluorescein and derivatives thereof, Rhodamine and derivatives thereof, dansyls and derivatives thereof (e.g. dansyl cadaverine). Texas red, eosin, cyanine dyes, indocarbocyanine, oxacarbocyanine, thiacarbocyanine, merocyanine, squaraines and derivatives Seta, SeTau, and Square dyes, naphthalene and derivatives thereof, coumarin and derivatives thereof, pyridyloxazole, nitrobenzoxadiazole, benzoxadiazole, anthraquinones, pyrene and derivatives thereof, oxazine and derivatives, Nile red, Nile blue, cresyl violet, oxazine 170, proflavin, acridine orange, acridine yellow, auramine, crystal violet, malachite green, porphin, phthalocyanine, bilirubin, tetramethylrhodamine, hydroxycoumarin, aminocoumarin; methoxycoumarin, Cascade Blue, Pacific Blue. Pacific Orange. NBD, R-phycoerythrin (PE), Red 613; PerCP, TruRed; FluorX. Cy2, Cy3, Cy5 and Cy7, TRITC, X-Rhodamine, Lissamine Rhodamine B, allophycocyanin (APC) and Alexa Fluor dyes.

Allergen families that can be detected using the detection system and device described herein include allergens from foods, the environment or from non-human proteins such as domestic pet dander. Food allergens include, but are not limited to proteins in legumes such as peanuts, peas, lentils and beans, as well as the legume-related plant lupin, tree nuts such as almond, cashew, walnut, Brazil nut, filbert/hazelnut, pecan, pistachio, beechnut, butternut, chestnut, chinquapin nut, coconut, ginkgo nut, lychee nut, macadamia nut, nangai nut and pine nut, egg, fish, shellfish such as crab, crawfish, lobster, shrimp and prawns, mollusks such as clams, oysters, mussels and scallops, milk, soy, wheat, gluten, corn, meat such as beef, pork, mutton and chicken, gelatin, sulphite, seeds such as sesame, sunflower and poppy seeds, and spices such as coriander, garlic and mustard, fruits, vegetables such as celery, and rice. The allergen may be present in a flour or meal, or in any format. For example, the seeds from plants, such as lupin, sunflower or poppy can be used in foods such as seeded bread or can be ground to make flour to be used in making bread or pastries.

In some embodiments, detection agents for eight major food allergens (i.e. wheat, egg, milk, peanuts, tree nuts, fish, shell-fish and soy) may be provided as disposables. In one aspect, constructs of the detection agents may be stored with MgCl, or buffer doped with KCl. MgCl keeps constructs closed tightly, while KCl opens them slightly for bonding.

Washing Process and Optical Read

In some embodiments, one or more washes may be performed during the allergen detection testing. The wash buffer stored in the chamber 522 is released to wash the mixture comprising the processed sample and detection agents before reading the optical signals from the reaction.

In some embodiments, aptamer-magnetic bead conjugates are used as the detection agents. As a non-limiting example, a washing process is performed following the steps (as shown in FIG. 21):

1. A food sample is introduced to the homogenization chamber 521 by the user;
2. Performing initial optical detection read on the dry and empty flow cell 1801 (the magnet bead collection area on the fluidic chip 1802 (or the glass cover 635) within the reaction chamber 524);
3. Releasing the pre-stored extraction buffer from the processing reservoir 901 in the homogenization chamber 521. In an alternative embodiment, if the extraction buffer is stored in a separate storage reservoir (e.g., an extraction buffer storage reservoir in the storage chamber 522), a valve between the storage chamber 522 and the homogenization chamber 521 (FIG. 21, valve 1), and a valve between the homogenization chamber 521 and the waste chamber 523 (FIG. 21, valve 5) are open, releasing the extraction buffer to the homogenization chamber 521;
4. (Optional) Activating the suction pump (pump 1540), pulling the extraction buffer to the waste chamber 523 when it is necessary to remove the extraction buffer;
5. Closing valve 1 and valve 5;
6. Collecting the detection agents, magnetic particles conjugated with aptamers which specifically bind to the target allergen; the magnetic beads are then retained in the flow cell 1801 by a magnetic force;
7. Opening the two valves (valve 2 and valve 4 as shown in FIG. 21) that locate between the reaction chamber 524 and the buffer storage chamber 522, and the waste chamber 523, respectively, allowing the wash buffer pre-stored in the wash buffer reservoir 902 in the storage chamber 522 to be filled into the reaction chamber (the flow cell 1801) to re-suspend the magnetic particles within the cell (the magnetic bead collection area);
8. Closing valve 2 and valve 4;
9. Mixing the magnetic particles with the wash buffer; an internal or external means may be used to sonicate/agitate the flow cell 1801 to promote the mixing;
10. Homogenizing the food sample and extracting allergen protein in the homogenization chamber 521;
11. Performing an optical detection read on the wetted and re-suspended flow cell 1801;
12. Collecting and retaining the magnetic particles by a magnetic force, keeping the magnetic particles which are resident in the flow cell, within the flow cell 1801;
13. Opening valve 3 between the homogenization chamber 521 and the reaction chamber 524 (the flow cell 1801) and valve 4;
14. Activating the suction pump (pump 1540), pulling the homogenized food sample solution (including extraction buffer) through a filter (filtrate) and into the flow cell 1801;
15. Filling the filtrate into the flow cell 1801;
16. Stopping the suction pump and closing all the valves;
17. Releasing the magnetic particles retained in the flow cell 1801 to mix with the filtrate: an internal or external means may be used to sonicate/agitate the flow cell 1801 to promote the mixing;
18. Performing an optical detection read on the flow cell 1801;
19. Collecting and retaining the magnetic particles by a magnetic force, keeping the magnetic particles within the flow cell 1801;
20. Opening valve 2 and valve 4;
21. Activating the suction pump, pulling the wash buffer through the flow cell 1801 until all the filtrate has been removed;
22. Stopping the suction pump and closing valve 2 and valve 4;
23. Releasing the magnetic particles to mix with the wash buffer; an internal or external means may be used to sonicate/agitate the flow cell 1801 to promote the mixing;
24. Reading the washed magnetic particles with the optical detection system;
25. (Optional) Repeating the washing cycle for some types of filtrate samples, if required; and 26. Reading again the washed magnetic particles with the optical detection system.

In some embodiments, a solid support (e.g., the glass cover 635, or a separate glass chip in lieu of the fluidic chip 1802 as shown in FIGS. 18A and 18B)) of which the surface is coated with aptamers specific to a target allergen (referred to as DNA surface plate) may be used as the detection agents. As a non-limiting example, a washing process is performed following the steps: I. A food sample is introduced to the homogenization chamber 521 by the user;

2. Performing initial optical detection read on the flow cell (the DNA surface plate within the reaction chamber 524);
3. Releasing the pre-stored extraction buffer from the processing reservoir 901 in the homogenization chamber 521. In an alternative embodiment, if the extraction buffer is stored in a separate storage reservoir (e.g., an extraction buffer storage reservoir in the chamber 522), valve 1 and valve 5 are open, releasing the extraction buffer to the homogenization chamber 521;
4. (Optional) Activating the suction pump (pump 1540), pulling the extraction buffer to the waste chamber 523 when it is necessary to remove the extraction buffer;
5. Closing valve 1 and valve 5;
6. Opening valve 2 and valve 4, filling the wash buffer pre-stored in the wash buffer reservoir 902 in the storage chamber 522 to the flow cell (i.e. the DNA surface plate) to wet the DNA surface plate;
7. Closing valve 2 and valve 4;
8. Sonicating/agitating the DNA surface plate with the wash buffer by an internal or external means to promote the wetting;
9. Homogenizing the food sample and extracting allergen protein in the homogenization chamber 521;
10. Performing an optical detection read on the wetted DNA surface plate;
11. Opening valve 3 and valve 4;
12. Activating the suction pump (pump 1540), pulling the homogenized food sample solution (including extraction buffer) through a filter (filtrate) and into the DNA surface plate;
13. Filling the filtrate into the DNA surface plate;
14. Stopping the suction pump and closing all the valves;
15. Sonicating/agitating the DNA surface plate by an internal or external means to promote diffusion;
16. Performing an optical detection read on the DNA surface plate;
17. Opening valve 2 and valve 4;
18. Activating the suction pump, pulling the wash buffer through the DNA surface plate until all the filtrate has been removed;
19. Stopping the suction pump and closing valve 2 and valve 4;
20. Sonicating/agitating the DNA surface plate by an internal or external means to promote diffusion;
21. Reading the DNA surface plate with the optical detection system;
22. (Optional) Repeating the washing cycle for some types of filtrate samples, if required: and
23. Reading again the DNA surface plate with the optical detection system.

Optical Signal Reads and Analysis

In one embodiment, the system of the present invention is operated to perform the assay for detecting the presence and/or absence of a target allergen in a food sample using DNA-magnetic beads conjugates as the detection agents. Prior to the assay, dry lyophilized magnetic beads contained in the dry reaction chamber 524 or suitable alternate locations are provided. The dry magnetic beads are first resuspended in the extraction buffer, followed by a first set of optical signals which include a fluorescence signal read from the magnetic beads alone ($S_b$), absorption read and scatter light read. The suspended magnetic beads are then pulled to the magnetic collection area (e.g., the flow cell 1801) which is the sensing area, by a magnetic force. A second set of optical signals including absorption and scatter light is read. After introducing the processed food sample from the homogenization chamber 521 to the reaction and signal detection chamber 524, a third set of optical signals including a fluorescence signal from the auto fluorescence background ($A_f$), absorbed light and scattered light is read. magnetic beads are then released from the magnetic force and re-suspended for reacting with the processed food sample. Post-reacted magnetic beads are again pulled to the magnetic collection area by the magnetic force. A fourth set of optical signals including a fluorescence signal, absorbed light and scattered light is read. A washing step is performed to wash off non-binding magnetic beads, food sample and extra buffer. The washing efficiency is recorded ($W_e$). After washing, the optical signals including a fluorescence signal, $S=(1-W_e)*A$, absorbed light and scattered light are read again. A final set of optical signals is obtained and processed including a fluorescence signal, $S=B_{loss}*(Sb-x)+(1-We)$, wherein $B_{loss}$ stands for bead loss after washing and x stands for signal drop after washing, absorbed light, expressed as ($B_{loss}$)(500), and scattered light. All the recorded optical signals and reference signals are then used to calculate the presence and/or absence of the target allergen.

Optical Reading of Magnetic Beads

In one example, lyophilized magnetic beads conjugated with aptamers specific to a target allergen are used as detection agents. In this context, optical signals in the reaction chamber 524 (FIGS. 5A and 5B) may be read following the steps of:
1. Reading the baseline with the absorption system prior to buffer introduction;
2. Reconstituting the agents with buffer; buffer is added and the beads are resuspended; optionally the magnetic beads may be stirred;
3. Reading the light absorption with the absorption optics 1830 (FIGS. 18A and 18B, and FIG. 19);
4. Reading the fluorescence signal and scattered light with the fluorescence optical systems 1810 and 1820, and the scatter optics 1840 (FIGS. 18A and 18B, and FIG. 19); the fluorescence reading may be compared against a pre-defined fluorescence level to insure sufficient signal is present;
5. Adding the processed food sample to the reaction chamber 524 while holding the beads with a magnetic force (i.e. the beads are gathered within the sensing area in the chamber); and promoting the chemical reaction between the target allergen present in the food sample and the detection agent;
6. Reading the light absorption with the absorption optics 1830, scattered light with the scatter optics 1840, and fluorescence signal with the fluorescence optical systems 1810 and 1820 (FIGS. 18A and 18B, and FIG. 19);
7. Washing out the food sample while the beads are kept compressed in the sensing area with the magnetic force;
8. Reading the light absorption with the absorption optics 1830, scattered light with the scatter optics 1840, and fluorescence signal with the fluorescence optical systems 1810 and 1820 (FIGS. 18A and 18B, and FIG. 19); and
9. Processing the fluorescence reading and reporting the detection result.

In step 3, a significant decrease (e.g., more than 90%) in signal is expected due to magnetic bead absorption. An insufficient decrease in signal may suggest that the buffer was not successfully injected into the reaction chamber 524 from the storage reservoir. Therefore, dry magnetic beads do not reconstitute. The system may adjust for repeating the reconstitution.

The baseline reading of fluorescence signal in step 4 will be compared with the reading of fluorescence signal after wash (step 8). The baseline scattered light reading in step 4 is for comparison with the scattered reading obtained when the food sample is injected into the reaction chamber 524 (Step 6).

In one aspect, prior to the addition of the processed food sample (step 5), a free dye may be added to the suspended dark magnetic beads at a concentration where the light intensity reading provides a signal level that the final read can be compared against. The comparison level may be used as one of the lot specific parameters for the test. For example, if the free dye reading is too low, the test may be terminated. In another aspect, a method of reading the background with buffer in the chamber and in the absence of the beads may be provided; the background reading would be subtracted from all future readings.

The absorption and scatter reading in step 6 may provide a verification to indicate that the food sample is injected into the reaction chamber 524.

The absorption reading in step 8 will be close to the starting absorption level, indicating the food sample has been washed out. If the absorption reading goes down, it may indicate that the beads have been washed off from the sensing area (out of the reaction chamber 524). If the absorption reading is significantly high, it may indicate that the food sample is not completely washed out of the reaction chamber 524. The scattered light reading in step 8 will be close to the starting scattered light level. If the scattered light level is significantly high, it may indicate that the food sample is not completely washed out of the reaction chamber 524. A verification method will be provided accordingly to adjust the detection process.

The fluorescence signal in step 8 is compared to the reading from previous steps. The measurements and the final readings will inform the consumer if the sample contains allergens (e.g., is safe to eat). In some cases, if the fluorescence signal from the tested sample itself is too high, a change of the fluorescence signal may not be read and the test may be terminated. In other cases, if the sample viscosity as measured by the rotor 540 (FIG. 6) and motor system 1510 (FIG. 15) of the detection device is too high for proper processing, the test may be stopped.

In accordance with the present invention, each reading of the optical signals may take place between 10 milliseconds to 1 second.

Optical Reading of a Chip

In some embodiments, a solid support (e.g., the glass cover 635 or a separate glass chip) is provided with a surface coated with aptamers specific to a target allergen (referred to as DNA surface plate) may be used as the detection agent. In this context, the DNA surface plate is used to replace the fluidic chip 1802 and is inserted into the reaction chamber 524 in the same area occupied by the fluidic chip 1802 (FIGS. 18A and 18B). Optical signals from the DNA surface plate in the reaction chamber 524 (FIGS. 5A and 5B) may be read following the steps of:
 1. Adding buffer to the reaction chamber 524;
 2. Reading the fluorescence signal of the test area (referred to as "unknown" area in FIG. 22A); the fluorescence reading of the test area is the background signal. If the background signal is too high, the process may be terminated;
 3. Reading the fluorescence signal of the two control areas (FIG. 22A); the fluorescence reading is compared against a baseline level to ensure sufficient signal is present;
 4. Adding the processed food sample to the reaction chamber 524 and allowing the chemical reaction between the target allergen present in the sample and the detection agent on the chip;
 5. Reading a set of fluorescence signals of the test area and the two control areas with the fluorescence optical systems 1810 and 1820 (FIGS. 18A and 18B, and FIG. 19);
 6. Washing out the sample;
 7. Reading a second set of fluorescence signals of the test area and the two control areas with the fluorescence optical systems 1810 and 1820 (FIGS. 18A and 18B, and FIG. 19);
 8. Processing the fluorescence reading and reporting the detection result.

Figure 22B:
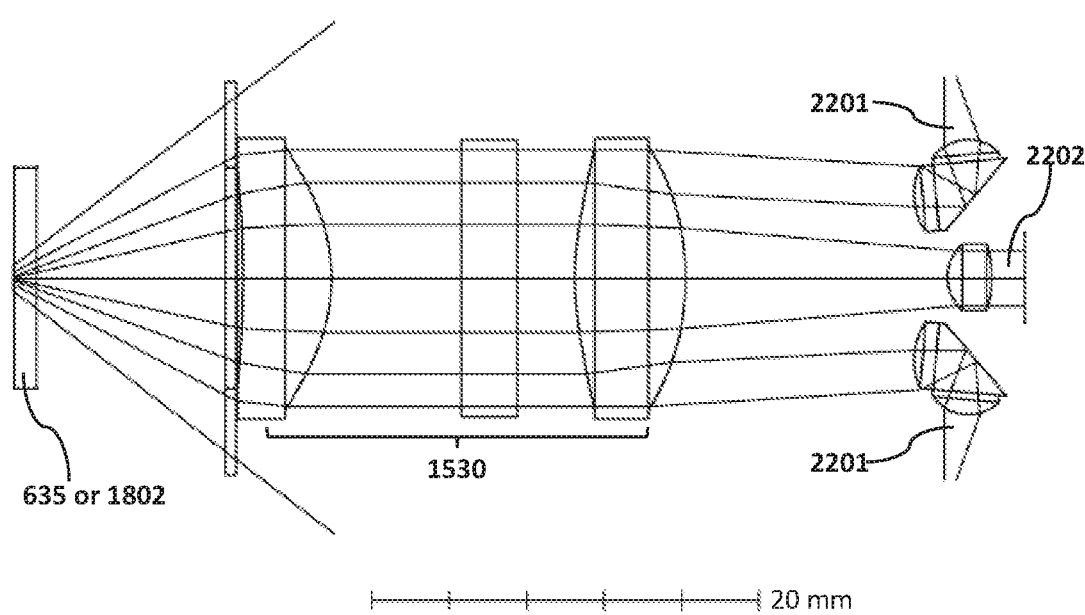
FIG. 22B depicts the fluorescence reading to detect the chip sensor (e.g., 635 or 1802).

In accordance with the present invention, the two control areas are constantly bright areas on the chip sensor that produce a constant signal as background signals 2201 (FIGS. 22A and 22B). In addition, the two control areas compensate for laser illumination and/or disposable cartridge misalignment. If the cartridge is perfectly aligned, then the fluorescence background signals 2201 would be equal (as shown in FIG. 22B). If the measured control signals are not equal, a look-up table of correction factors is used to correct the unknown signal as a function of cartridge/laser misalignment. The final read is a comparison of the signal 2202 of the unknown test area against the signal levels of the control areas. The comparison level may be one of the lot-specific parameters for the test.

Food samples with high background fluorescence readings from the test area (step 5) may produce a false negative result. A verification method may be provided to adjust the process.

An increase in the fluorescence reading of the control areas in step 7 may indicate that the food sample is not completely washed out. Additional wash mechanisms may be added before reading the fluorescence signal again. If the increase is not too high, a delta modulation in signal is used to compensate the fluorescence reading in the test area. If the increase is too high, the detection test may be terminated.

The final fluorescence reading of the test area, after being compared to the controls and any lot specific parameters may be analyzed, and a report is provided to the consumer if the sampled food is safe to eat.

Accordingly, the light absorption and scatter signal may also be read at the baseline level, before and/or after the injection of the processed food sample. These readings will provide additional parameters to adjust the detection assay. For example, the scatter signal may also be measured with the scatter optics 1840. Such signal may be used to determine if residual food sample remains in the reaction chamber 524 after the wash step.

In addition to the parameters discussed above, one or more other lot specific parameters may also be measured. The optimization of the parameters, for example, may minimize the disparity in the control and unknown signal levels for the chips.

Applications

The detection systems, devices and methods described herein contemplate the use of nucleic acid-based detector molecules such as aptamers for detection of allergens in food samples. The portable devices allow a user to test the presence or absence of one or more allergens in food samples. Allergen families that can be detected using the device described herein include allergens from legumes such as peanuts, tree nuts, eggs, milk, soy, spices, seeds, fish, shellfish, wheat gluten, rice, fruits and vegetables. The allergen may be present in a flour or meal. The device is capable of confirming the presence or absence of these allergens as well as quantifying the amounts of these allergens.

In a broad concept, the detection systems, devices and methods described herein may be used for detection of any protein content in a sample in a large variety of applications in addition to food safety, such as, for example, medical diagnosis of diseases in civilian and battlefield settings, environmental monitoring/control and military use for the detection of biological weapons. In even broad applications, the detection systems, devices and methods of the present invention may be used to detect any biomolecules which nucleic acid-based detector molecules bind. As non-limiting examples, the detection systems, devices and methods may be used for on the spot detection of cancer markers, in-field diagnostics (exposure to chemical agents, traumatic head injuries etc.), third-world applications (TB, HIV tests etc.), emergency care (stroke markers, head injury etc.) and many others.

As another non-limiting example, the detection systems, devices and methods of the present invention can detect and identify pathogenic microorganisms in a sample. Pathogens that can be detected include bacteria, yeasts, fungi, viruses and virus-like organisms. Pathogens cause diseases in animals and plants; contaminate food, water, soil or other sources, or are used as biological agents in military fields. The device is capable of detecting and identifying pathogens.

Another important application includes the use of the detection systems, devices and methods of the present invention for medical care, for example, to diagnose a disease, to stage a disease progression and to monitor a response to a certain treatment. As a non-limiting example, the detection device of the present invention may be used to test the presence or absence, or the amount of a biomarker associated with a disease (e.g. cancer) to predict a disease or disease progression. The detection systems, devices and methods of the present invention are constructed to analyze a small amount of test sample and can be implemented by a user without extensive laboratory training.

Other expanded applications outside of the field of food safety include in-field use by military organizations, testing of antibiotics and biological drugs, environmental testing of products such as pesticides and fertilizers, testing of dietary supplements and various food components and additives prepared in bulk such as caffeine and nicotine, as well as testing of clinical samples such as saliva, skin and blood to determine if an individual has been exposed to significant levels of an individual allergen.

Kits

Kits comprising one or more disposable cartridges of various embodiments as described herein are provided for use with embodiments of the detection device described herein. Such kits include instructions for preparation and placement of the disposable cartridges with respect to the detection device. Such kits may also include instructions for obtaining background readings and performing various calibration tasks and allergen measurement readings as described herein.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above description, but rather is as set forth in the appended claims.

A number of possible alternative features are introduced during the course of this description. It is to be understood that, according to the knowledge and judgment of persons skilled in the art, such alternative features may be substituted in various combinations to arrive at different embodiments of the present invention.

Any patent, publication, internet site, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

EXAMPLES

Example 1: Optical Reading of Aptamer-Magnetic Bead Conjugates

Figure 23A:
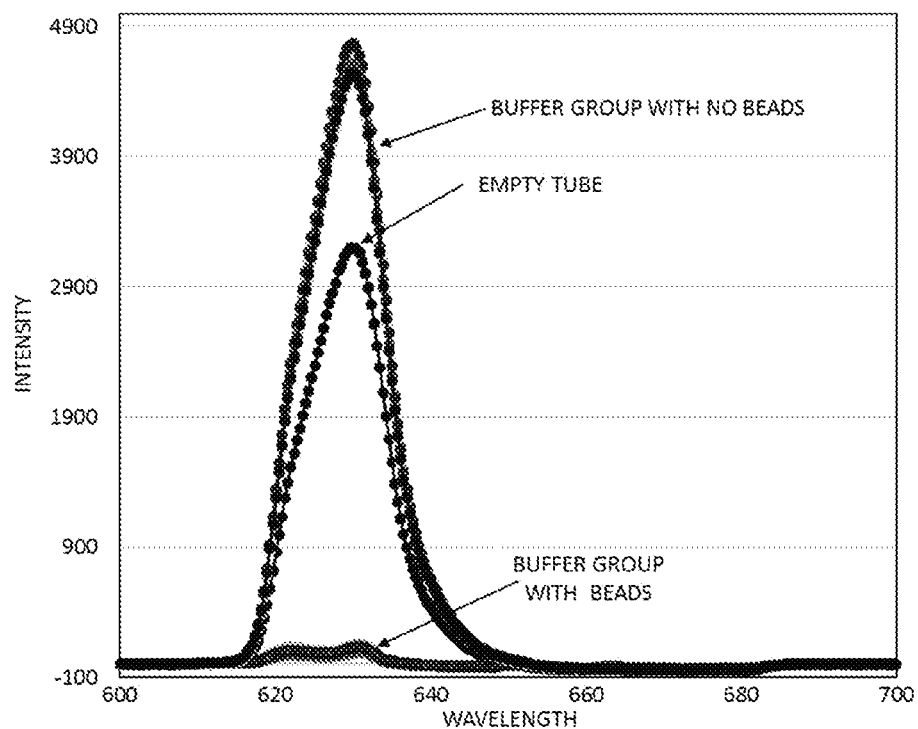
FIG. 23A displays series of absorption spectra of buffer, an empty tube and buffer containing magnetic beads.

Magnetic bead conjugates in buffer at a concentration of 1.67 µg/µL and buffer alone were tested for light absorption. The conjugates were labeled with Texas Red dye. The data suggests that magnetic beads can dramatically decrease optical read (FIG. 23A).

Figure 23B:
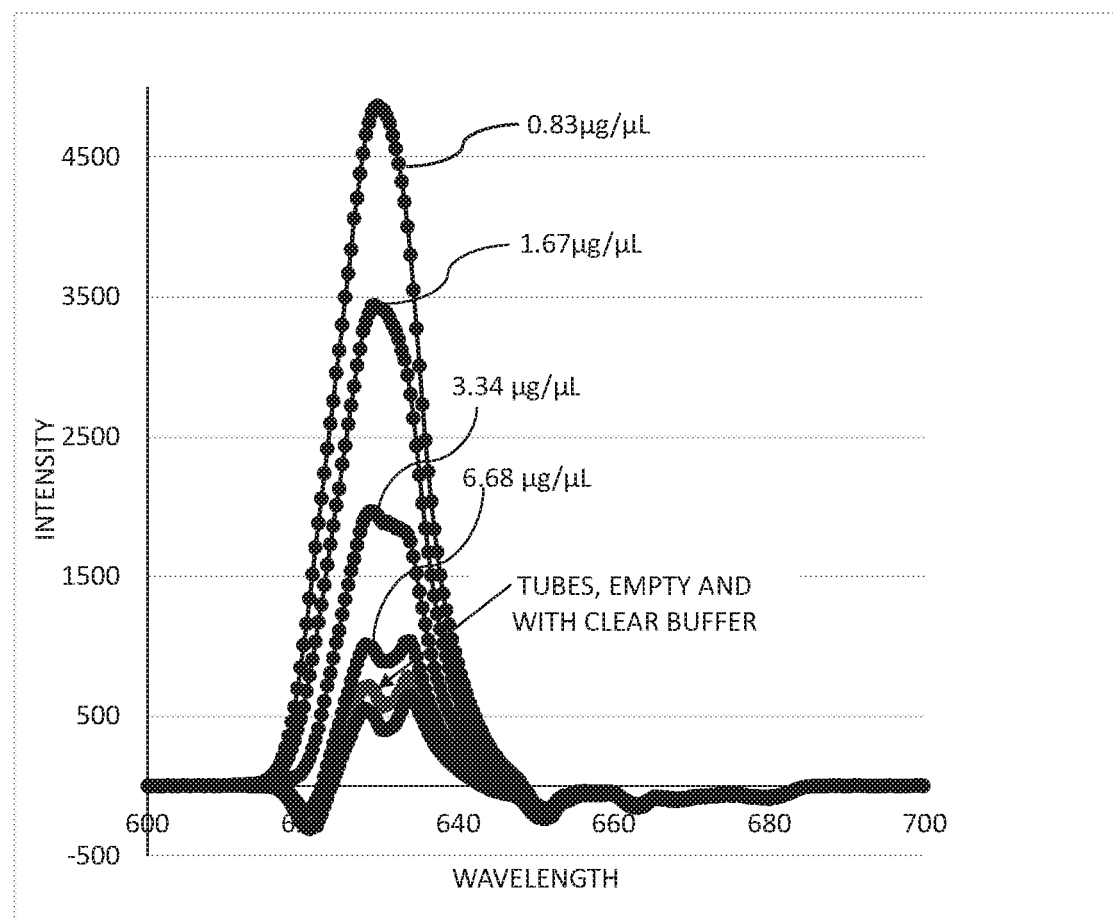
FIG. 23B displays a series of scattered light spectra of magnetic beads at various concentrations in milk buffer.

Scattered light was read for various samples: magnetic beads alone, beads with buffer, and beads at various concentrations mixed with food samples (milk buffer). The scattered light results suggest that light scattering varies in different mixtures. As shown in FIG. 23B, the two curves at the bottom indicate light scattering detected for an empty tube (Cepheid, Calif., USA) and a tube with clear buffer. The top four lines in FIG. 23B indicate the scattered light readings for mixtures of magnetic beads with milk. Four different concentrations of magnetic beads (0.83 µg/µL, 1.67 µg/µL, 3.34 µg/µL and 6.68 µg/µL, respectively) were mixed with 10 nM milk buffer.

The invention claimed is:

1. A detection system for detecting the presence or absence of an allergen in a food sample, comprising:
   (a) a food corer for collecting the food sample suspected of containing said allergen;
   (b) a disposable test cup configured for processing the food sample and contacting detection agents with said allergen presented in the food sample, the test cup comprising a port for inserting the food corer; and
   (c) a detection device configured for operating an allergen detection test and measuring signals from a binding interaction between the detection agents and said allergen and visualizing a detection result, the device having a mate plane for docking the disposable test cup,
   wherein the detection device comprises an optical system for measuring said signals, the optical system comprising excitation optics, emission optics, scatter optics and/or absorption optics;
   wherein the disposable test cup (b) comprises:
      (i) a cup top cover;
      (ii) a cup body;
      (iii) a cup bottom assembly; and
      (iv) a homogenization rotor;
      wherein the cup bottom assembly provides interfaces for connecting to the mate plane of the detection device; and
   wherein the cup body (ii) comprises a plurality of chambers, each of which is functionally connected and a fluid can flow from one chamber to another, wherein the cup body comprises at least:
      (1) a homogenization chamber, wherein the food sample is homogenized and allergen proteins are extracted;
      (2) a washing chamber wherein a processed sample solution and/or a mixture of the food sample and detection agents are washed;
      (3) a waste chamber configured for holding waste that accumulates while the allergen detection test is being performed; and
      (4) a reaction and optical detection chamber wherein reaction signals and reference signals are read.

2. The detection system of claim 1, wherein the food corer comprises:
   a plunger at the distal end of the food corer;
   a skirt; and
   a corer at the proximal end of the food corer,
   wherein the proximal end of the corer comprises a cutting edge for cutting the food sample.

3. The detection system of claim 1, wherein the reaction and optical detection chamber further comprises magnetic beads conjugated with nucleic acid molecules that specifically bind to the target allergen, or a solid support having a surface coated with nucleic acid molecules that specifically bind to the target allergen.

4. The detection system of claim 3, wherein the nucleic acid molecules are aptamers or aptamer-complement complexes which bind to the target allergen with high specificity and affinity.

5. The detection system of claim 3, wherein the solid support is selected from a group consisting of a glass chip, silica, agarose beads, acrylic glass, a microwell and a microchip.

6. The detection system of claim 3, wherein the reaction and optical detection chamber further comprises a first optical window and a second optical window, wherein the first optical window and second optical window are aligned with the optical system of the detection device when the test cup is docked into the detection device.

7. The detection system of claim 1, wherein the homogenization rotor is inserted into the test cup body (ii) through either a rotor interface at the cup bottom assembly (iii) or a rotor port at the cup top cover (i).

8. The detection system of claim 1, wherein the test cup further comprises a filter that comprises a filter membrane or a filter assembly.

9. A detection system for detecting the presence or absence of an allergen in a food sample, comprising:
   (a) a food corer for collecting the food sample suspected of containing said allergen;
   (b) a disposable test cup configured for processing the food sample and contacting detection agents with said allergen presented in the food sample, the test cup comprising a port for inserting the food corer;
   (c) a detection device configured for operating an allergen detection test and measuring signals from a binding interaction between the detection agents and said allergen and visualizing a detection result, the device having a mate plane for docking the disposable test cup,
   (d) an external housing configured for providing support for components of the detection device;
   (e) components integrated for operating an allergen detection test; and
   (f) a power supply;
   wherein the detection device comprises an optical system for measuring said signals, the optical system comprising excitation optics, emission optics, scatter optics, and/or absorption optics;
   wherein the components integrated for operating the allergen detection test comprise:
      (i) a motor for driving and controlling a homogenization rotor in the disposable test cup;
      (ii) a pump for driving and controlling flow of a processed sample solution during the allergen detection test;
      (iii) at least one magnetic collection actuator for collecting and retaining magnetic beads;
      (iv) a vibratory re-suspension actuator for re-suspending magnetic beads;

(v) a system for converting and digitizing fluorescence signals; and
(vi) a display window for receiving the fluorescence signals and indicating the presence and/or absence of the allergen in the food sample.

10. The detection system of claim 9, wherein the excitation optics of the optical system comprise:
(1) a light source having a light spectral range configured to transmit an excitation light to an optical detection chamber;
(2) one or more excitation filters configured to select specific excitation wavelengths of light from the light source, wherein at least three different light wavelength bands are selected, comprising:
(i) an absorption band for determining the presence of detection agents in the optical detection chamber, wherein the detection agents are magnetic particles coated with signal polynucleotides (SPNs);
(ii) a scatter band for detecting light scattered off the food sample inside the optical detection chamber; and
(iii) a fluorescence band configured to detect a fluorescence signal derived from the binding interaction of the allergen of interest and SPNs; and
(3) optional optics capable of confining the light path; and
wherein the emission optics of the optical system comprise:
(1) one or more emission filters operable to allow substantially only light with wavelengths in an emission band to reach the detector;
(2) optional optics configured to collect and confine emitted light; and
(3) a detector capable of measuring signals from the food sample, wherein the scatter optics are operable to measure scattered light signals.

11. The detection system of claim 9, wherein the magnetic bead collection actuator further comprises:
(1) a magnetic field generator which generates a magnetic field to hold and separate magnetic beads; and
(2) an actuator,
wherein the magnetic field generator comprises a permanent magnet or an electromagnet.

12. A method for detecting the presence or the absence of an allergen in a food sample comprising:
(a) collecting and processing the food sample, wherein the food sample is homogenized and proteins from the food sample are extracted in an extraction buffer;
(b) reading a baseline set of absorption, scatter, and fluorescence signals in an optical detection chamber;
(c) transferring the processed food sample into an optical detection chamber within a disposable cup, wherein the optical detection chamber is preloaded with detection agents,
wherein the detection agents comprise magnetic beads coated with aptamers which are labeled with one or more fluorophores, or a glass chip having a surface coated with aptamers which are labeled with one or more fluorophores;
(d) mixing the processed food sample with the detection agents within the optical detection chamber to form a mixture;
(e) reading a first set of absorption, scatter and fluorescence signals;
(f) washing out unbound compounds from the mixture;
(g) reading a second set of absorption, scatter and fluorescence signals;
(h) comparing the following sets of signals:
(i) the first set of absorption, scatter, and fluorescence signals from step (e);
(ii) the second set of absorption, scatter and fluorescence signals of step (f); and
(iii) the baseline set of absorption, scatter and fluorescence signals from step (b); and
(i) detecting the presence or absence of the allergen in the food sample based on the comparison of step (h).

13. The method of claim 12, wherein the detection agent is the glass chip, and wherein the fluorescence signals comprise signals from a test area and two control areas of the glass chip.

14. A system for detecting the presence of an allergen in a sample, the system comprising:
(a) a device comprising: an optical system configured to measure absorbed light, scattered light or fluorescence or a combination thereof, as a result of binding of a detection agent to the allergen;
b) a test cartridge configured to dock into a receptacle of the device, the test cartridge comprising:
(i) a homogenization chamber comprising a rotor for homogenizing the sample and extracting allergens;
(ii) a wash buffer chamber;
(iii) a waste chamber configured to receive liquid waste; and
(iv) a reaction and optical detection chamber in optical communication with the optical system, for detecting the binding of the detection agent to the allergen.

15. The system of claim 14, wherein the reaction and optical detection chamber further comprises magnetic beads conjugated with nucleic acid molecules that specifically bind to the target allergen, or a solid support having a surface coated with nucleic acid molecules that specifically bind to the target allergen.

16. The system of claim 15, wherein the nucleic acid molecules are aptamers or aptamer-complement complexes which bind to the target allergen with high specificity and affinity.

17. The system of claim 15, wherein the solid support is selected from the group consisting of: a glass chip, silica, agarose beads, acrylic glass, a microwell and a microchip.

18. The system of claim 14, wherein the reaction and optical detection chamber further comprises a first optical window and a second optical window, wherein the first optical window and second optical window are aligned with the optical system of the detection device when the cartridge is docked into the receptacle of the device.

19. The system of claim 14, wherein the rotor is mechanically connected to a rotor-driving motor at an interface on the bottom of the test cartridge.

20. The system of claim 14, wherein the homogenization chamber comprises extraction buffer and the wash buffer chamber comprises wash buffer.

21. The system of claim 20, wherein the homogenization chamber and the wash buffer chamber each have passages with lower openings having seals which, when broken, permit fluid flow into a lower flow channel for transfer of homogenized sample and wash buffer from the homogenization chamber to the reaction and optical detection chamber.

22. The system of claim 15, wherein the device comprises a magnet which is movable between a first position and a second position,
wherein the first position is for attracting the magnetic beads to an interior wall of the reaction and optical detection chamber, and wherein the second position is for allowing dispersal of the magnetic beads throughout the interior of the reaction and optical detection chamber.

23. The system of claim 14, wherein the optical system is configured to measure absorbed light, scattered light and fluorescence with a single detector, and
   wherein the absorbed light indicates the presence of magnetic beads and/or sample in the reaction and optical detection chamber, the scattered light indicates the presence of sample in the chamber, and the fluorescence indicates detection of the allergen.

24. The system of claim 21, further comprising valves at the entrance and the exit of the reaction and optical detection chamber,
   wherein the entrance is at the end of the lower flow channel, and
   wherein the exit leads to the waste chamber.

25. The system of claim 14, wherein a drive mechanism for the rotor is located in the device below the receptacle.

26. The system of claim 14, wherein the test cartridge comprises an upper opening configured for insertion of a sampling device, the sampling device configured for addition of a sample to the homogenization chamber.

27. The system of claim 14, further comprising a sampling device configured for insertion into an upper opening of the test cartridge, for addition of a sample to the homogenization chamber.

28. The system of claim 15, wherein the device further comprises a magnetic bead resuspension actuator in the receptacle, the resuspension actuator configured for contacting the cartridge to effect resuspension of the magnetic beads.

29. The system of claim 28, wherein the magnetic bead resuspension actuator is a vibratory actuator.

* * * * *